United States Patent
Rubin et al.

(10) Patent No.: US 10,323,009 B2
(45) Date of Patent: Jun. 18, 2019

(54) METHODS AND COMPOSITIONS FOR GAMMA-GLUTAMYL CYCLE MODULATION

(71) Applicant: Cancer Research Technology, LLC, Las Vegas, NV (US)

(72) Inventors: David Rubin, San Diego, CA (US); Eyal Rubin, San Diego, CA (US)

(73) Assignee: CANCER RESEARCH TECHOLOGY, LLP, Las Vegas, NV (US)

( * ) Notice: Subject to any disclaimer, the term of this patent is extended or adjusted under 35 U.S.C. 154(b) by 0 days.

(21) Appl. No.: 15/495,496

(22) Filed: Apr. 24, 2017

(65) Prior Publication Data

US 2017/0226070 A1  Aug. 10, 2017

Related U.S. Application Data

(62) Division of application No. 14/214,888, filed on Mar. 15, 2014, now Pat. No. 9,630,936.

(60) Provisional application No. 61/801,709, filed on Mar. 15, 2013.

(51) Int. Cl.
  *A61K 31/426* (2006.01)
  *C07D 277/06* (2006.01)
  *C07D 277/04* (2006.01)

(52) U.S. Cl.
  CPC .......... *C07D 277/06* (2013.01); *A61K 31/426* (2013.01); *C07D 277/04* (2013.01); *C07B 2200/13* (2013.01)

(58) Field of Classification Search
  CPC .................................................. A61K 31/426
  See application file for complete search history.

(56) References Cited

U.S. PATENT DOCUMENTS

| | | | |
|---|---|---|---|
| 3,773,919 A | 11/1973 | Boswell et al. | |
| 4,011,233 A | 3/1977 | Dubs et al. | |
| 4,775,675 A | 10/1988 | Gyorgydeak et al. | |
| 5,169,858 A | 12/1992 | Rubin | |
| 5,385,922 A | 1/1995 | Bron et al. | |
| 8,889,881 B2 | 11/2014 | Chung et al. | |
| 2004/0229819 A1* | 11/2004 | Kowalczyk .......... | C07D 207/04 546/189 |
| 2006/0014740 A1 | 1/2006 | Miller et al. | |
| 2006/0110814 A1 | 5/2006 | Srivastava et al. | |
| 2007/0155807 A1 | 7/2007 | Miller et al. | |
| 2008/0176923 A1 | 7/2008 | Salama | |
| 2008/0220441 A1 | 9/2008 | Birnbaum et al. | |
| 2009/0105286 A1 | 4/2009 | Famulok et al. | |
| 2009/0233972 A1 | 9/2009 | Or et al. | |
| 2010/0144606 A1 | 6/2010 | Connolly et al. | |
| 2011/0092501 A1 | 4/2011 | Heiser et al. | |

FOREIGN PATENT DOCUMENTS

| | | |
|---|---|---|
| JP | 56/133216 A * | 10/1981 |
| JP | 57/128625 A * | 8/1982 |
| WO | WO 1992/04337 | 3/1992 |
| WO | WO 2005/035527 A1 | 4/2005 |
| WO | WO 2005/037257 A2 | 4/2005 |
| WO | WO 2007/044515 | 4/2007 |
| WO | WO 2012/108689 A2 | 8/2012 |

OTHER PUBLICATIONS

An English machine translation of JP 57-128625 A (Takeuchi et al.), 1982.*
An English machine translation of JP 56-133216 A (Ogata et al.), 1981.*
Brand, Udo et al. Zinc Complexes of S, N Ligands Derived from Thiazolines, Chemische Berichte, (Aug. 1, 1995), vol. 128, No. 8, p. 787-791.
Chemical Abstracts Registry No. 280108-21-6, indexed in the Registry file on STN CAS Online Jul. 25, 2000.
Chemical Abstracts Registry No. 280108-25-0, indexed in the Registry file on STN CAS Online Jul. 25, 2000.
Chemical Abstracts Registry No. 786657-99-6, indexed in the Registry file on STN CAS Online Nov. 23, 2004.
Chemical Abstracts Registry No. 829-36-7, indexed in the Registry file on STN CAS Online Nov. 16, 1984.
Extended European Search Report and Supplementary European Search Report in European Application No. 14763483.6, dated Jan. 11, 2017, in 13 pages.
Franklin, Michael et al., Pre- and Post-Initiation Chemoprevention Activity of 2-alkyl/aryl Selenazolidine-4(R)-Carboxylic Acids Against Tobacco-Derived Nitrosamine (NNK)-Induced Lung Tumors in the A/J mouse, Chemicobiological Interactions, (Jun. 27, 2007) vol. 168, No. 3, p. 211-220.
Gyorgydeak, Zoltan et al., Darstellung and Charakterisierung Von Diastereomerene (4S)-3-Acetyl-2-aryl-5,5-dimethyl-4-thiazolidincarbonsauren, Liebigs Annalen der Chemie, 1990, 3, pp. 281-286.
International Search Report and Written Opinion in International Application No. PCT/US14/30053, dated Sep. 19, 2014, in 15 pages.
Konigsmann, Michael al., Fludarabine and Bendamustine in Refractory and Relapsed Indolent Lymphoma-a Multicenter Phase I/II Trial of the East German Society of Hermatology and Oncology (OSHO), Leuk. Lymphoma, 2004; 45(9):1821-1827.
Nicolaou et al., "Calicheamicin ΘI1: A rationally designed molecule with extremely potent and selective DNA cleaving properties and apoptosis inducing activity," Angew. Chem. Intl. Ed. Engl., Feb. 1, 1994, 33(2):183-186.
Peng, Li-Jun et al., N-Nitrosation of (E)-2-(benzylideneamino)ethanols, Tetrahedron Letters, (Sep. 14, 2007),7418-7421.

(Continued)

*Primary Examiner* — Laura L Stockton
(74) *Attorney, Agent, or Firm* — Duane Morris LLP

(57) ABSTRACT

The present disclosure provides pharmaceutical compositions comprising Gamma-glutamyl cycle inhibitors (GGCI) and certain pharmaceutically acceptable salts thereof, and methods of use.

6 Claims, 4 Drawing Sheets

(56) References Cited

OTHER PUBLICATIONS

Pessoa, Joao Costa et al., N-Salicylideneamino Acidato Complexes of Oxovanadium(IV). The Cysteine and Penicillamine Complexes, Dalton Transactions: The International Journal for Inorganic, Organometallic and Bioinorganic Chemistry, (Jan. 1, 2004), No. 18, p. 2855-2866.

Tsukuda, Mamoru et al., Phase I Trial of Combined Chemotherapy with Docetazel, Cisplatin, and 5-Fluorouracil for Patients with Locally Advanced Squamous Cell Carcinoma of the head and Neck, Int. J. Clin. Oncol. Jun. 2004; 9(3):161-6.

Wondrak, Georg et al., Identification of alpha-docarbonyl sacevengers for Cellular Protection Against Carbonyl Stress, Biochemical Pharmacology, (Feb. 1, 2002), vol. 63, No. 3, p. 361-373.

* cited by examiner

Synthesis schemes of exemplary GGCI

METHODS AND COMPOSITIONS FOR GAMMA-GLUTAMYL CYCLE MODULATION

RELATED APPLICATION

This application is a divisional application of U.S. application Ser. No. 14/214,888, filed on Mar. 15, 2014 which will issue as U.S. Pat. No. 9,630,936 on Apr. 25, 2017 and claims priority to U.S. Provisional Application Ser. No. 61/801,709, entitled Methods And Compositions For Gamma-Glutamyl Cycle Modulation, filed Mar. 15, 2013, the contents of which are herein incorporated by reference as if set forth in their entirety.

FIELD

The present disclosure is generally related to novel compounds of the general formula I and pharmaceutically acceptable salts or esters thereof. The present disclosure also relates to pharmaceutical compositions containing them, methods of making the above compounds, and their use as gamma-glutamyl cycle inhibitors (GGCI), which are useful in the treatment or prevention of diseases, particularly malignancies, complications related to malignancies, and other pathogenic conditions in which the gamma-glutamyl cycle (GGC) is implicated. In particular, the disclosure provides methods and compositions for the treatment of malignancies by modulating the gamma-glutamyl cycle and the de novo biosynthesis of glutathione.

BACKGROUND

The following includes information that may be useful in understanding various aspects and embodiments of the present disclosure. It is not an admission that any of the information provided herein is prior art, or relevant, to the presently described or claimed inventions, or that any publication or document that is specifically or implicitly referenced is prior art.

The gamma-glutamyl cycle (GGC) (FIG. 2) is a biosynthetic pathway that is present in almost every living cell. It enables the transport of amino acids, transferrin, iron, and other moieties from outside a living cell, through the cell membrane, into the cytoplasm. Some of the amino acids are essential for the de novo biosynthesis of glutathione. The GGC for the biosynthesis of glutathione. The GGC does not require insulin as a cofactor.

Glutathione (GSH) biosynthesis is catalyzed by γ-glutamylcysteine synthetase (GGCS) and glutathione synthetase (GS), two enzymes in the gamma-glutamyl cycle. The cellular cysteine concentration and GGCS levels are rate-limiting. GGCS is feedback inhibited by GSH, leading to a steady state in cellular GSH.

Gamma-glutamyl transpeptidase (GGT) catalyzes two reactions: hydrolysis of a γ-glutamyl bond and transpeptidation (TP). GGT is induced to high levels in many pre-neoplastic lesions (altered hepatic foci, AHF) at early stages of hepatocarcinogenesis (HC) in rodents. The ubiquity of elevated GGT levels in many rodent and human hepatic and extrahepatic carcinomas have led to the hypothesis that GGT provides a growth advantage to focal cells during carcinogenesis. Because GGT participates in detoxification of xenobiotics, the growth advantage has been suggested to result from resistance to the acute toxicity of carcinogens.

SUMMARY OF THE INVENTION

Although there are many established therapeutic agents directed to cancer therapy, it was recognized by the inventors that the novel stereoisomeric compounds of this disclosure are useful as cancer therapeutics.

The present disclosure provides synthetic methods, novel analogs of 5-oxoproline, and pharmaceutical formulations and kits comprising the analogs. The compounds and pharmaceutical formulations are useful for cancer therapeutics that target 5-oxoprolinase, an enzyme in the gamma-glutamyl cycle. Blocking of the enzyme 5-oxoprolinase blocks cell division of hyperproliferative cells, such as cancer cells, by interfering with the transport of essential amino acids into the cell and the synthesis of glutathione and other biosynthesis products of the gamma-glutamyl cycle. The methods and compositions are useful for controlling tumor progression, drug resistance and drug targeting. Accordingly, the disclosure provides methods of synthesizing and using modulators/inhibitors of the gamma-glutamyl cycle and of the de novo biosynthesis of glutathione, which are useful in the treatment of malignancies. Specifically, the compositions and methods of use thereof are provided to disrupt the conversion of 5-oxoproline to glutamic acid by 5-oxoprolinase.

In one aspect, the present disclosure provides a stereoisomeric compound represented by formula (I):

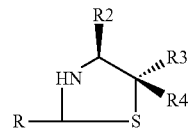

or an ester and/or pharmaceutically acceptable salt thereof, wherein:
  R is independently selected from optionally substituted aryl, heteroaryl, para-methoxyphenyl, methyl carbonyl, 2,6-dimethyl-1,5-heptadienyl, 2,6-dimethyl-5-heptenyl, ortho-hydroxy phenyl, phenyl, and 3-aldehyde-propyl;
  $R_2$ is independently selected from the group consisting of H, COOH; glucose esters, and glucuronic acid esters;
  $R_3$ and $R_4$ are independently selected from H, methyl or lower alkyl; and
  S is independently selected from the group consisting of optionally substituted sulfur, selenium, tellurium, or oxygen.

The compounds of formula I can be used in the methods of this invention as described herein. R may be obtained by the reaction of a suitable aldehyde in the methods of synthesis described herein. The aldehyde may be, for example, any substituted aryl-CHO or heteroaryl-CHO, pyruvic aldehyde, citral, citronellal, salicyl aldehyde, benzaldehyde, glutaric dialdehyde, or p-methoxybenzaldehyde.

In some embodiments, R and S are as described above, and $R_2$ is independently selected from the group consisting of COOH; glucose esters, and glucuronic acid esters, and $R_3$ and $R_4$ are independently selected from methyl or lower alkyl. In some embodiments, $R_2$ is COOH, and $R_3$ and $R_4$ are H. In some embodiments, where R3 and R4 are H, R is not ortho-hydroxyphenyl. In some embodiments, R2 can be COOR5, where R5 is a lower alkyl ester. In that embodiment, where R3 and R4 are methyl, and R is ortho-hydroxyphenyl, R5 is not methyl.

In one embodiment, the present disclosure relates to a compound and salts, and crystals, and polymorphs thereof, having the formula (II):

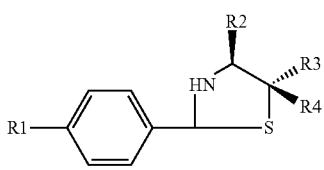

wherein the $R_1$ is —OCH3, and $R_2$, $R_3$, and $R_4$. are as above for formula (I). In one embodiment, the compound or salts, crystals, and polymorphs thereof, having the formula (III), also referred to herein as PMB-GGCI or MBDTA:

Formula III

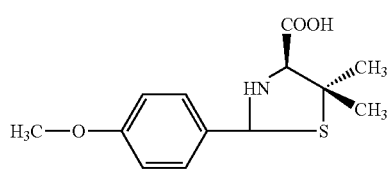

In one embodiment, the present disclosure relates to a compound and salts, crystals, and polymorphs thereof, having the formula (IV), also referred to herein as SA-GGCI when R2 is COOH and R3 and R4 are methyl:

Formula IV

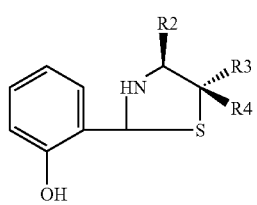

In one embodiment, the present disclosure relates to a compound and salts, and crystals, and polymorphs thereof, having the formula (V), also referred to herein as BA-GGCI when R2 is COOH and R3 and R4 are methyl:

Formula V

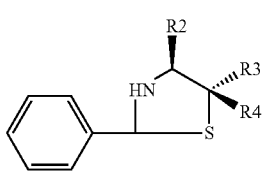

In the compounds of this invention, the carbon to which the carboxyl group is attached is in the (L) conformation. Reference to (L) and (D) compounds of this disclosure herein refers to the stereochemical conformation at the carbon adjacent to the R2 group in the compounds of Formula I-V or the carbon adjacent to the COOH group in Formula III. In one embodiment, when the p-methoxy benzyl ring is unsubstituted, the compound is (1L)-2-imino-3-p-methoxybenzyl-4 sulfanyl-5,5 dimethyl 1-carboxylic acid, which is alternatively named or (4L)-3-imino-2-p-methoxybenzyl-1 sulfanyl-5,5 dimethyl 4-carboxylic acid, or (4L)-2-p-methoxybenzyl-5,5-dimethyl-4-thiazolidinecarboxylic acid (MBDTA). In one embodiment, the compounds of this disclosure may be obtained by conjugating 3,3 dimethyl-(L)-cysteine, i.e., (L)-penicillamine, other (L)-cysteine analogs or cystamine with a suitable aldehyde to generate the stereoisomeric compounds of this invention.

In some embodiments the S atom in the heterocyclic ring can be replaced with selenium, telurium or oxygen. In one embodiment the thiazolidine ring has a dimethyl substituent for optimal activity. In another embodiment, the 5 position of the thiazolidine ring is substituted with a methyl and a hydrogen.

D-penicillamine (often referred to as penicillamine) is a drug used to remove copper in patients, for example in patients with Wilson's Disease, a genetic disorder of copper metabolism. Certain aldehyde conjugates of D-penicillamine have been described for use as copper-chelating inhibitors of tyrosinase. See U.S. Pat. No. 5,169,858.

However, in contrast to D-penicillamine, the L-penicillamine stereoisomer is toxic, and has not been approved as a drug. It was therefore suprisingly found by the inventors that the (L)-gamma-glutamyl cycle inhibitors (GGCIs) of this disclosure exhibit unexpected low toxicity. In certain embodiments, the inventors surprisingly discovered that when L-isomers of penicillamine were used as a starting material, the resultant GGCI synthesized using the synthetic scheme as described herein resulted in high yield synthesis of compounds having potent efficacy, and low toxicity, whereas the use of D-isomers of penicilalmine as starting material yielded compounds having no efficacy. More specifically, it was suprisingly found by the inventors that the (L) conformation compounds of this invention exhibited surprisingly high levels of anti-cancer activity in animal models and in compassionate use treatment of human subjects, while the (D) conformation compounds had minimal or no activity. For example, the inventors observed that (L)-MBDTA has potent anti-tumor activity while the (D) stereoisomer has no activity. Moreover, when the inventors compared the relative activities, the (L) conformation compounds of this disclosure appeared to be at least 2× as active as the corresponding racemate, due to the improved stereospecificity in the enzymatic catalysis of 5-oxoproline by 5 oxoprolinase.

In one aspect, the present disclosure provides a pharmaceutical composition comprising any GGCI disclosed herein and a pharmaceutically acceptable excipient. In another aspect, the present disclosure provides a composition for selectively treating tumor cells comprising an effective amount of a 5-oxoproline analog, whereby the analog is transported into the cell and binds to, but is not metabolized by, 5-oxoprolinase. The compounds of this invention are effective in inhibiting the synthesis of glutamic acid in the gamma-glutamyl cycle. In one embodiment, the composition inhibits the production of substrate for glutathione-S-transferase. In one embodiment, the composition inhibits glutathione-S-transferase comprised of 2-imino-3-p-methoxybenzyl-4 sulfanyl-5 dimethyl 1-carboxylic acid. In one embodiment, the composition comprises a GGCI salt and polymorphs thereof. In one embodiment, an isolated GGCI chloride salt that has a purity range selected from the group consisting of 50%, 55%, 60% pure, 65%, 70%, 75%, 80%, 85%, 90%, 95%, 98%, 99% or 100% pure is provided. In one embodiment, a substantially pure GGCI anhydrate, dihydrate, trihydrate, or tetrahydrate is provided. In one embodiment, a composition comprising a substantially pure GGCI crystal having alternating layers of GGCI molecules and mesylate molecules (mesylate salt), and a pharmaceutically acceptable carrier is provided.

In one aspect, the present disclosure provides the use of a compound of any of formulas I-V for the preparation of a medicament for the treatment of a condition selected from the group consisting of cancer, hyperplasia, and neoplasia. In one embodiment, the MDR is thereby inhibited and/or reduced. In one embodiment, the tumor progression is thereby inhibited and/or reduced. In one embodiment, the exemplary compounds bind sugar moieties and/or have high affinity lectin activity.

In one aspect the present disclosure provides a method of treating cancer comprising administering to a subject in need thereof a therapeutically effective amount of a pharmaceutical composition comprising a GGCI of formulas I-V, whereby gamma-glutamyl cycle is inhibited. In one embodiment, the GGCI is a 5-oxoproline analog. In one embodiment, the 5-oxoproline analog is 2-imino-3-p-methoxybenzyl-4 sulfanyl-5,5 dimethyl 1-carboxylic acid. In one embodiment, inhibition of the GGC results from the inhibition of biosynthesis by the GGC, for example, the inhibition of production of a product, an intermediate, or a metabolite of the GGC pathway.

In one embodiment, the level of glutathione is reduced in cancer cells. In one embodiment, the compounds of this invention inhibit glutathione-S-transferase, for example, by inhibiting production of its substrate. Glutathione protects cells from oxidative stress, including detoxifying reactive alkylating agents and oxidizing agents, and helps to block the damaging effects of therapeutic alkylating agents and/or oxidizing agents on cancer cells. In certain embodiments, the GGCI can be administered synergistically with an alkylating agent and/or oxidizing agents that can increases the risk/damage to cancer cells. In certain embodiments, the GGCIs of this invention can be administered in combination with an inhibitor of glutathoine-S-transferase to synergistically inhibit the GGC. For example, any of the compounds of this invention can be advantageously administered simultaneously and/or sequentially with tumeric extract and/or tacrinic acid. In certain embodiments, the GGCI can be used to prevent or diminish resistance to one or more cancer therapeutics, and/or to reduce the metabolic breakdown of alkylating and/or oxiding cancer therapeutics, permitting lowering of the dose and reduction of side effects.

In one aspect, the effective dose of GGCI is from 2 to 5 g/kg, for example, 4 g/kg. In another aspect, the effective dose of GGCI is given in one or more doses of 3.5 g/kg for each dose. In certain embodiments, the one or more effective doses of GGCI are administered subcutaneously. In one embodiment, the one or more effective doses of GGCI are administered intravenously. In one embodiment, the one or more effective doses of GGCI are administered intramuscularly. In one embodiment, the one or more effective doses of GGCI are administered orally. In one embodiment, the cancer is a solid tumor. In one embodiment, the treatment comprises treatment of solid tumors. In one embodiment, the tumors comprises sarcomas, carcinomas or lymphomas. In one embodiment, the cancer is selected from the group consisting of: lung, breast, prostate, pancreatic, ovarian, bladder, head and neck, thyroid, brain, skin and kidney. In one embodiment, the dose is administered by a delivery route selected from the group consisting of intraperitoneal, intradermal, intramuscular, intraperitoneal, intravenous, topical, subcutaneous, intranasal, oral, or epidural routes.

In one aspect, the present disclosure provides a method of synthesizing the compound of formula I, and salts thereof, wherein the compound is obtained by: the synthesis scheme of FIG. 1. In one embodiment, (L)-2-imino-3-p-methoxybenzyl-4 sulfanyl-5 dimethyl 1-carboxylic acid was synthesized. In one embodiment, equimolar quantities of methoxy toluene (p-methoxybenzaldehyde), di-methyl cysteine and manganese dioxide were dissolved in two liters of 70% ethanol. In one embodiment, the mixture was made in a rotary evaporator and the temperature was raised to 70° C. In one embodiment, after about 1 hour, all the ingredients dissolved. In one embodiment, the volume was then reduced by one liter. In one embodiment, the solution was left in the flask to cool down overnight to room temperature. In one embodiment, the precipitating white crystals of GCI were filtered and then dried in a vacuum oven after one day. In one embodiment, the disclosure provides intermediates for said synthesis scheme of FIG. 1.

In other embodiments, the appropriate substituted cysteine, cystamine and aldehyde may be reacted in the synthetic schemes of FIG. 1 to obtain the desired compound. The aldehyde may be, for example, any substituted aryl-CHO or heteroaryl-CHO, pyruvic aldehyde, citral, citronellal, salicylaldehyde, benzaldehyde, glutaric dialdehyde, or p-methoxylbenzaldehyde. In one embodiment, the (L)-isomer of cysteine or substituted cysteine (or a tellurium or oxygen analog thereof) is used as a starting reactant to obtain an enantiomer of the compound of formula (I) having a specific stereochemistry at the carbon to which the R2 group, or the carboxylic acid group, is attached. Exemplary reactants can include (L)-penicillamine, (L)-cysteine, and cystamine.

According to one aspect of the present invention, there are provided novel compounds represented by the general formula (I), their racemates, their pharmaceutically acceptable salts, and pharmaceutical compositions containing them, or mixture thereof.

In another aspect, the present invention provides a process for the preparation of novel organic compounds of the general formula (I), their racemates, their pharmaceutically acceptable salts, and pharmaceutical compositions containing them.

A further aspect of the present invention is to provide novel intermediates, a process for their preparation, and their use in methods of making compounds of the general formula (I).

In one embodiment, the present disclosure is related to the stereomeric compounds of the general formula I, their esters, racemates, and pharmaceutically acceptable salts thereof, wherein R is independently selected from optionally substituted aryl, heteroaryl, para-methoxyphenyl, methyl carbonyl, 2,6-dimethyl-1,5-heptadienyl, 2,6-dimethyl-5-heptenyl, 2-hydroxy phenyl, phenyl, and 3-aldehyde-propyl; R2 is independently selected from the group consisting of COOH; and esterified glucose or glucuronic acid; R3 and R4 are independently selected from methyl or lower alkyl; and S is independently selected from the group consisting of optionally substituted sulfur, selenium tellurium or oxygen. In some instances, when salicylaldehyde (SA) or benzaldehyde (BA) is used to obtain the exemplary Formula I-V compounds of this invention, a synergistic analgesic effect may also be obtained when treating subjects by administering those compounds according to the methods herein. In some embodiments, the exemplary compounds of formulae I-V can also be synthesized using exemplary starting compounds, such as, for example, (L)-penicillamine, (L)-cysteine, and cystamine.

In one aspect, this disclosure provides a method of treatment comprising administering to a subject in need thereof an effective amount of a pharmaceutical composition comprising GGCI.

In one embodiment, the subject has a solid tumor cancer. In another aspect, the solid tumor comprises sarcomas, carcinomas or lymphomas. In another embodiment, the cancer is selected from the group consisting of: lung, breast, prostate, pancreatic, ovarian, bladder, head and neck, thyroid, brain, liver, gallbladder, skin, colon, and kidney. In one embodiment, the solid tumor is a poorly reoxygenating tumor.

In one aspect, each dose of GGCI is between about 1 ng/kg and less to about 10 g/kg, and said dose is administered by a delivery route selected from the group consisting of intraperitoneal, intradermal, intramuscular, intramuscular, intravenous, parenteral, intranasal, intracranial, topical, subcutaneous, oral, and epidural routes.

The inventions described and claimed herein have many attributes and embodiments, including, but not limited to, those set forth, or described, or referenced, in this Brief Summary. It is not intended to be all-inclusive and the inventions described and claimed herein are not limited to, or by the features or embodiments identified in, this Brief Summary, which is included for purposes of illustration only and not restriction. Additional embodiments may be disclosed in the Detailed Description below.

BRIEF DESCRIPTION OF THE FIGURES

FIG. 3A is the control group after 120 days. FIG. 3B is the treated group after 120 days.

FIG. 4A is the control group after 120 days. FIG. 4B is the treated group after 120 days.

DETAILED DESCRIPTION

Figure 1:
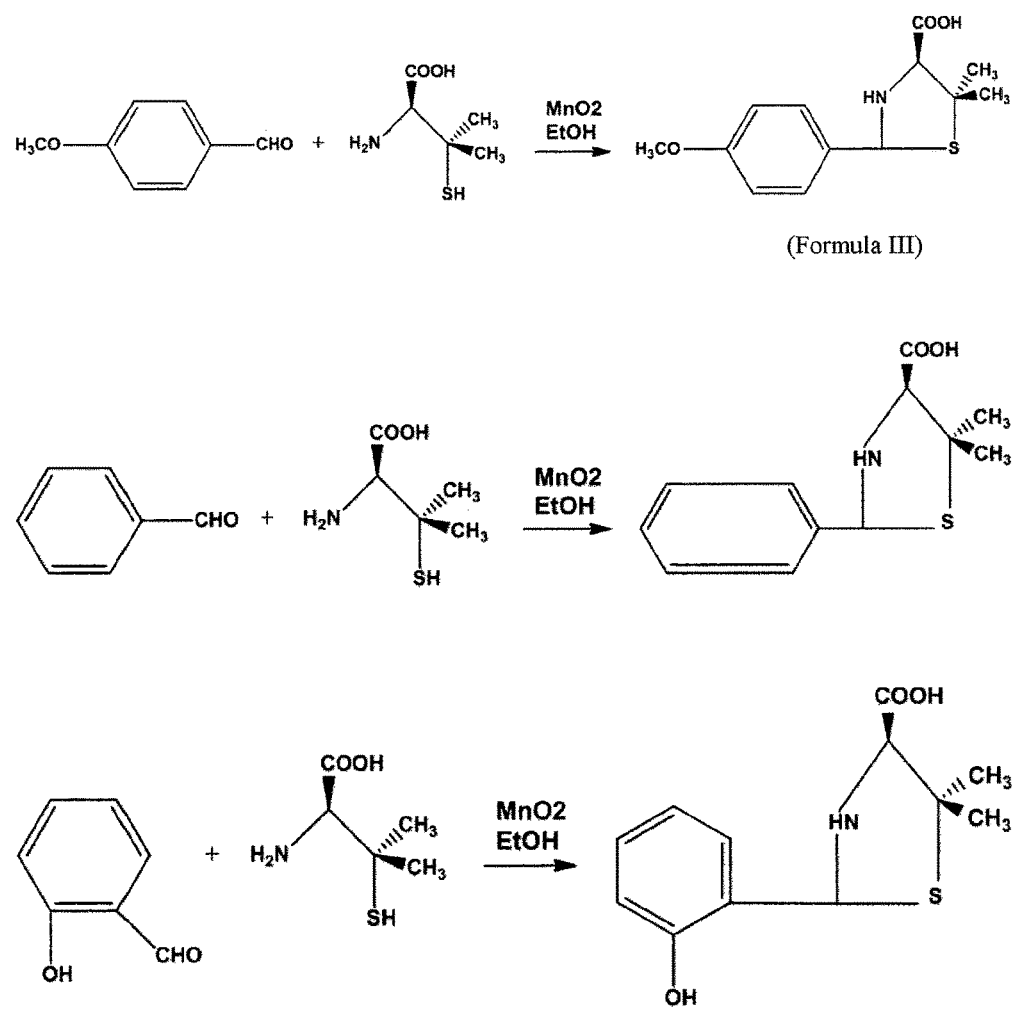
FIG. 1 depicts representative synthetic schemes for making exemplary GGCI/5-oxoproline analogs.

Accordingly, the present disclosure relates generally to novel gamma-glutamyl cycle inhibitors. The disclosure is based on the higher activity of the enzyme gamma-glutamyl transpeptidase found in cancerous cells and the substantially faster dividing rate of cancerous cells compared to cells of the non-cancerous origin. Inhibition of the GGC, for example, by blocking and/or interfering with one or more enzymes of the GGC, can lead to suppression of cancer cell growth and reduction in the number of cancer cells. The inhibition of the GGC can be achieved by presenting a "false metabolite" competitive inhibitor of an enzyme in the gamma-glutamyl cycle, which preferentially effects rapidly dividing cells, such as cancer cells. By doing so, the GGCI of this disclosure can have more deleterious effects on cancer cells than to the non-cancerous cells.

In one aspect, this disclosure relates to the synthesis of the novel inhibitors of this disclosure that compete with 5-oxoproline for binding 5-oxoprolinase, thereby reducing and/or inhibiting biosynthesis by other enzymes in the gamma-glutamyl cycle through substrate depletion. This blocks GGC mediated amino acid transport into the cell and interferes with cell division. In addition, the GGCIs of this invention further interfere with GGC synthesis of glutathione. Since cancerous cells need substantially more amino acids to support a much faster doubling time than non-cancerous cells, the GGCIs of this invention will preferentially damage cancerous cells.

Definitions

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. The term alkyl further includes alkyl groups, which comprise oxygen, nitrogen, sulfur, or phosphorous, atoms replacing one or more carbons of the hydrocarbon backbone. The term "aromatic-alkyl" includes alkyl groups substituted with one or more aryl groups. The term "lower alkyl" as used herein refers to [3 or fewer carbons].

The term "aryl" includes groups with aromaticity, including 5- and 6-membered single-ring aromatic groups that may include from zero to four heteroatoms, as well as multicyclic systems with at least one aromatic ring. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenyl aminocarbonyl, alkylcarbonyl, arylcarbonyl, aralkyl carbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused, or bridged, with alicyclic or heterocyclic rings which are not aromatic, so as to form a multicyclic system (e.g., tetralin, methylenedioxyphenyl).

The term "alkylene" refers to divalent saturated aliphatic groups and includes both straight chain and branched chain groups.

The term "alkenylene" refers to divalent aliphatic groups having a double bond and includes both straight chain and branched chain groups.

As used herein, a "subject" refers to an animal that is the object of treatment, observation or experiment. "Animal" includes cold- and warm-blooded vertebrates and invertebrates, such as fish, shellfish, reptiles and, in particular, mammals. "Mammal" includes, without limitation, mice; rats; rabbits; guinea pigs; dogs; cats; sheep; goats; cows; horses; primates, such as monkeys, chimpanzees, apes, and prenatal, pediatric, and adult humans.

As used herein, "preventing" or "protecting" means preventing in whole or in part, or ameliorating, or controlling.

As used herein, the term "treating" refers to both therapeutic treatment and prophylactic, or preventative, measures, or administering an agent suspected of having therapeutic potential. The term includes preventative (e.g., prophylactic) and palliative treatment.

The term "a pharmaceutically effective amount", as used herein, means an amount of active compound, or pharmaceutical agent, that elicits the biological, or medicinal, response in a tissue, system, animal, or human that is being sought, which includes alleviation or palliation of the symptoms of the disease being treated and/or an amount sufficient to have utility and provide desired therapeutic endpoint. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, e.g., by assessing the time to disease progression and/or determining the response rate.

The term "pharmaceutically acceptable", as used herein, means that the substance or composition must be compatible chemically and/or toxicologically, with the other ingredients comprising a formulation, and/or the mammal being treated therewith.

The term "cancer" refers to, or describes, the physiological condition in mammals that is typically characterized by unregulated cell growth and/or hyperproliferative activities. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer, including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer, regardless of mechanism of action. Classes of chemotherapeutic agents include, but are not limited to: alkyating agents, antimetabolites, spindle poison plant alkaloids, cytoxic/antitumor antibiotics, topoisomerase inhibitors, antibodies, photosensitizers, and kinase inhibitors. Chemotherapeutic agents include compounds used in "targeted therapy" and conventional chemotherapy. Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine,dichloroplatinum(II), CAS No. 15663-27-1), carboplatin (CAS No. 41575-94-4), paclitaxel (TAXOL®, Bristol-Myers Squibb Oncology, Princeton, N.J.), pemetrexed (ALIMTA®, Eli Lilly), trastuzumab (HERCEPTIN®, Genentech), temozolomide (4-methyl-5-oxo-2,3,4,6,8-pentazabicyclo[4.3.0]nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorphosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gamma1I, calicheamicin omega1I (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate, or inhibit, hormone action on tumors, such as anti-estrogens and selective estrogen receptor modulators (SERMs), including, e.g., tamoxifen (including NOLVADEX®; tamoxifen citrate), raloxifene, droloxifene, 4-hydroxytamoxifen, trioxifene, keoxifene, LY117018, onapristone, and FARESTON® (toremifene citrate); (ii) aromatase inhibitors that inhibit the enzyme aromatase, which regulates estrogen production in the adrenal glands, such as, e.g., 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, e.g., PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, e.g., ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG™, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents, in combination with the gamma-glutamyl inhibitors of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

A "metabolite" is a product produced through metabolism in the body of a specified compound, or salt thereof. Metabolites of a compound may be identified using routine techniques known in the art, and their activities determined, using tests such as those described herein. Such products may result e.g., from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms, or groups, in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures, such as electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that the compounds of this invention have the (L)-conformation at the carbon adjacent to the R2 group in the compounds of Formula I and II, and the carbon adjacent to the COOH group in Formula III.

Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). For amino acids and derivatives thereof, the D and L nomenclature has been traditionally used to designate the conformation at the chiral carbon adjacent to the carboxyl group. The prefixes d and l or (+) and (−) may be employed to designate the sign of rotation of plane-polarized light by the compound, with (−) or l meaning that the compound is levorotatory. A compound prefixed with (+) or d is dextrorotatory. For a given chemical structure, these stereoisomers are identical, except that they are mirror images of one another. A specific stereoisomer may also be referred to as an enantiomer, and a mixture of such isomers is often called an enantiomeric mixture. A 50:50 mixture of enantiomers is referred to as a racemic mixture, or a racemate, which may occur where there has been no stereoselection, or stereospecificity in a chemical reaction or process. The terms "racemic mixture" and "racemate" refer to an equimolar mixture of two enantiomeric species, devoid of optical activity.

The phrase "pharmaceutically acceptable salt" as used herein, refers to pharmaceutically acceptable organic, or inorganic, salts of a compound of the invention. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis(2-hydroxy-3-naphthoate)) salts. A pharmaceutically acceptable salt may involve the inclusion of another molecule, such as an acetate ion, a succinate ion, or other counter ion. The counter ion may be any organic, or inorganic, moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, e.g., treatment of the free base with an inorganic acid, such as hydrochloric acid, hydrobromic acid, sulfuric acid, nitric acid, methanesulfonic acid, phosphoric acid and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, e.g., treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

A "solvate" refers to an association, or complex, of one or more solvent molecules and a compound of the invention. Examples of solvents that form solvates include, but are not limited to, water, isopropanol, ethanol, methanol, DMSO, ethylacetate, acetic acid, and ethanolamine.

Administration of Formula I Compounds

The Formula I compounds of the invention may be administered by any route appropriate to the condition to be treated. Suitable routes include intraperitoneal (IP), oral, parenteral (including subcutaneous, intramuscular, intravenous, intraarterial, intradermal, intrathecal and epidural), transdermal, rectal, nasal, topical (including buccal and sublingual), vaginal, intrapulmonary and intranasal. For local immunosuppressive treatment, the compounds may be administered by intralesional administration, including perfusing or otherwise contacting the graft with the inhibitor before transplantation. It will be appreciated that the preferred route may vary with, e.g., the condition of the recipient. Where the compound is administered orally, it may be formulated as a pill, capsule, tablet, etc., with a pharmaceutically acceptable carrier or excipient. Where the compound is administered parenterally, it may be formulated with a pharmaceutically acceptable parenteral vehicle, and in a unit dosage injectable form, as detailed below.

A dose to treat human patients may range from about 10 mg to about 1000 mg of Formula I compound. The dose may be from about 20 mg, 25 mg, 30 mg, 40 mg, 50 mg, 60 mg, 70 mg, 75 mg, 80 mg, 90 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg of a Formula I compound, or any dose ranging between any two of those doses. In some instances, for example, where L cysteine or cystamine or other compounds suitable for use as food supplements are used to obtain Formula I compounds of this invention, the doses may also be from about 20 mg, 25 mg, 30 mg, 40 mg, 50 mg, 60 mg, 70 mg, 75 mg, 80 mg, 90 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1500 mg, 2000 mg, 2500 mg, 3000 mg, 3500 mg, 4000 mg, 4500 mg, 5000 mg, 5500 mg, 6000 mg, 6500 mg, 7000 mg, 7500 mg, 8000 mg, 8500 mg, 9000 mg, 9500 mg, or about 10,000 mg, or any dose ranging between any two of those doses, for example from about 100 mg to about 10,000 mg. A typical dose may be about 100 mg to about 600 mg tid of the compound. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. A typical dose when administered orally, the pill, capsule, or tablet may be ingested daily or less frequently for a specified period of time. The regimen may be repeated for a number of cycles of therapy.

Methods of Treatment with Formula I Compounds

Formula I compounds of the present invention are useful for treating hyperproliferative diseases, conditions and/or disorders including, but not limited to, cancer. Accordingly, an aspect of this invention includes methods of treating, or preventing, diseases or conditions that can be treated or prevented by inhibiting GGC. In one embodiment, the method comprises administering to a subject, in need thereof, a therapeutically effective amount of a compound of Formula I, or a stereoisomer, enantiomer, geometric isomer, tautomer, or pharmaceutically acceptable salt thereof. In one embodiment, a human patient is treated with a compound of Formula I and a pharmaceutically acceptable carrier, adjuvant, or vehicle, wherein said compound of Formula I is present in an amount to detectably inhibit GGC activity.

Cancers which can be treated according to the methods of this invention include, but are not limited to, breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukemia.

Formula I compounds may be useful for in vitro, in situ, and in vivo diagnosis or treatment of mammalian cells, organisms, or associated pathological conditions, such as hyperproliferative disease and/or cancer.

Formula I compounds may be useful for treating conditions of the brain and central nervous system which require transport across the blood-brain barrier. Certain Formula I compounds have favorable penetrant properties for delivery to the brain. Disorders of the brain which may be effectively treated with Formula I compounds include metastatic and primary brain tumors, such as glioblastoma and melanoma.

Formula I compounds may be useful for treating eye cancers by localized delivery to the eye. Certain Formula I compounds have favorable properties for delivery to, and uptake into, the eye. Certain Formula I compounds may enhance efficacy and extend duration of response for treatment of wet AMD in combination with ranibizumab (LUCENTIS®, Genentech, Inc.) and bevacizumab (AVASTIN®, Genentech, Inc.).

Another aspect of this invention provides a compound of this invention for use in the treatment of the diseases or conditions described herein in a subject, e.g., a human, suffering from such disease or condition. Also provided is the use of a compound of this invention in the preparation of a medicament for the treatment of the diseases and conditions described herein in a warm-blooded animal, such as a mammal, e.g. a human, suffering from such disorder.

Pharmaceutical Formulation/Compositions and Uses

In order to use a Formula I compound for the therapeutic treatment (including prophylactic treatment) of mammals including humans, it is normally formulated in accordance with standard pharmaceutical practice as a pharmaceutical composition. According to this aspect of the invention, there is provided a pharmaceutical composition comprising a compound of this invention in association with a pharmaceutically acceptable diluent or carrier.

A typical formulation is prepared by mixing a Formula I compound and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the Formula I compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, a compound of Formula I having the desired degree of purity may optionally be mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compound of this invention for use herein is preferably sterile. In particular, formulations to be used for in vivo administration must be sterile. Such sterilization is readily accomplished by filtration through sterile filtration membranes.

The compound ordinarily can be stored as a solid composition, a lyophilized formulation or as an aqueous solution (e.g. in saline).

The pharmaceutical compositions of the invention comprising a Formula I compound will be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. In addition to the compounds and salt forms provided herein, the invention includes pharmaceutical compositions, including tablets, capsules, solutions, and suspensions for parenteral and oral delivery forms and formulations, comprising a pharmaceutically acceptable carrier and therapeutically effective amounts of one or more of the GGCI compounds herein provided. GGCI pharmaceutical compositions can include salts and hydrates.

In human and animal therapy for the treatment of cancer, for example in the treatment of cancer and other related disorders, diseases and conditions noted herein, the compounds and their crystal forms described and provided herein, their pharmaceutically acceptable salts, and pharmaceutically acceptable solvates of either entity, can be administered alone, but will generally be administered in admixture with a pharmaceutical carrier selected with regard to the intended route of administration and standard pharmaceutical practice. Preferably, they are administered orally in the form of tablets containing pharmaceutically acceptable excipients, such as starch or lactose, or in capsules or ovules either alone or in admixture with excipients, or in the form of elixirs, solutions or suspensions containing flavouring or colouring agents. They can also be injected parenterally, for example, intravenously, intramuscularly or subcutaneously. For parenteral administration, they are best used in the form of a sterile aqueous solution which may contain other substances, for example enough salts or monosaccharides to make the solution isotonic with blood. For buccal or sublingual administration they may be administered in the form of tablets or lozenges which can be formulated in a conventional manner.

As a general proposition, the initial pharmaceutically effective amount of the Formula I compound administered parenterally per dose will be in the range of about 0.01-100 mg/kg, 0.01-1.0, 1.0 to 10.0, or 10.0 to 100.0 mg/kg. The amount of the Formula I compound administered parenterally per dose may also be about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include saline and/or buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, e.g., by coacervation techniques or by interfacial polymerization, e.g., hydroxymethylcellulose or gelatin-microcapsules and poly-(methylmethacylate) microcapsules, respectively, in colloidal drug delivery systems (e.g., liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations of Formula I compounds may be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (e.g., poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula I suitable for oral administration may be prepared as discrete units such as pills, capsules, cachets or tablets each containing a predetermined amount of a compound of Formula I.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula I intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, e.g., inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations may be applied as a topical ointment or cream containing the active ingredient(s) in an amount of, e.g., 0.075 to 20% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions of this invention may be constituted from known ingredients in a known manner. While the phase may comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of Formula I compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula I may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, about 0.5 to 10% w/w, or about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising, e.g. cocoa butter or a salicylate.

Formulations suitable for intrapulmonary or nasal administration have a particle size e.g. in the range of 0.1 to 500 microns (including particle sizes in a range between 0.1 and 500 microns in increments microns such as 0.5, 1, 30 microns, 35 microns, etc.) which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, e.g. sealed ampoules and vials, and may be stored in a freeze-dried (lyophilized) condition requiring only the addition of the sterile liquid carrier, e.g., water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of Formula I may be employed alone, or in combination with other therapeutic agents, for the treatment of a disease or disorder described herein, such as a hyperproliferative disorder (e.g., cancer). In certain embodiments, a compound of Formula I is combined in a pharmaceutical combination formulation, or dosing regimen as combination therapy, with a second compound that has anti-hyperproliferative properties or that is useful for treating a hyperproliferative disorder (e.g., cancer). The second compound of the pharmaceutical combination formulation or dosing regimen preferably has complementary activities to the compound of Formula I such that they do not adversely affect each other. Such compounds are suitably present in combination in amounts that are effective for the purpose intended. In one embodiment, a composition of this invention comprises a compound of Formula I, in combination with a chemotherapeutic agent such as described herein.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other chemotherapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes, separate pills or capsules, or separate infusions. In general, during alternation therapy, an effective dosage of each active ingredient is administered sequentially, i.e., serially, whereas in combination therapy, effective dosages of two or more active ingredients are administered together.

In a particular embodiment of anti-cancer therapy, a compound of Formula I, or a stereoisomer, geometric isomer, tautomer, solvate, metabolite, or pharmaceutically acceptable salt or prodrug thereof, may be combined with other chemotherapeutic, hormonal or antibody agents such as those described herein, as well as combined with surgical therapy and radiotherapy. Combination therapies according to the present invention thus comprise the administration of at least one compound of Formula I, or a stereoisomer, geometric isomer, tautomer, solvate, metabolite, or pharmaceutically acceptable salt or prodrug thereof, and the use of at least one other cancer treatment method. The amounts of the compound(s) of Formula I and the other pharmaceutically active chemotherapeutic agent(s) and the relative timings of administration will be selected in order to achieve the desired combined therapeutic effect.

Metabolites of Formula I Compounds

Also falling within the scope of this invention are the in vivo metabolic products of Formula I described herein. Such products may result, e.g., from the condensation, oxidation, reduction, hydrolysis, amidation, deamidation, esterification, deesterification, enzymatic cleavage, and the like, of the administered compound. Accordingly, the invention includes metabolites of compounds of Formula I, including compounds produced by a process comprising contacting a compound of this invention with a mammal for a period of time sufficient to yield a metabolic product thereof.

Metabolite products typically are identified by preparing a radiolabelled (e.g., 14C or 3H) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, may be useful in diagnostic assays for therapeutic dosing of the compounds of the invention.

Articles of Manufacture/Kits

In another embodiment of the invention, an article of manufacture, or "kit", containing materials useful for the treatment of the diseases and disorders described above is provided. The kit comprises a container comprising a compound of Formula I. The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, e.g., bottles, vials, syringes, blister pack, etc. The container may be formed from a variety of materials such as glass or plastic. The container may hold a compound of Formula I or a formulation thereof which is effective for treating the condition and may have a sterile access port (e.g., the container may be an intravenous solution bag or a vial having a stopper pierceable by a hypodermic injection needle). At least one active agent in the composition is a compound of Formula I. The label or package insert indicates that the composition is used for treating the condition of choice, such as cancer. In addition, the label or package insert may indicate that the patient to be treated is one having a disorder such as a hyperproliferative disorder. In one embodiment, the label or package inserts indicates that the composition comprising a compound of Formula I can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula I and, if present, the second pharmaceutical formulation. For example, if the kit comprises a first composition comprising a compound of Formula I, and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula I, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, e.g. in the form of numbers, letters, or other markings or with a calendar insert, designating the days in the treatment schedule in which the dosages can be administered.

According to one embodiment, a kit may comprise (a) a first container with a compound of Formula I contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of Formula I and a second therapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

The invention includes an article of manufacture comprising packaging material containing one or more dosage forms containing a GGCI compound provided herein, wherein the packaging material has a label that indicates that the dosage form can be used for a subject having or suspected of having or predisposed to any of the diseases, disorders and/or conditions described or referenced herein. Such dosage forms include, for example, tablets, capsules, solutions and suspensions for parenteral and oral delivery forms and formulations.

In yet another aspect of this invention is a kit comprising (a) at least one GGCI compound, or salt or crystal thereof, and a pharmaceutically acceptable carrier, excipient and/or additive in a unit dosage form, and (b) means for containing the unit form. Since the present invention has an aspect that relates to the treatment of the disease/conditions described herein with a combination of active ingredients, the invention also relates to combining separate pharmaceutical compositions in kit form. A kit may contain a pharmaceutical composition comprising GGCI compound, or salt or crystal thereof, as provided herein, either alone or together with a second compound as described herein.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

GGCI Agents

By following the procedures and synthetic schemes described in the Detailed Description of the Invention and the Examples and using methods and synthetic procedures known to those of skilled in the art, the salts and compositions of the present invention may be made.

The present methods also provide certain compounds that have utility, for example, as intermediates for synthesis of GGCI. Intermediates may be independently isolated and purified and/or crystallized, including during, and as a part of, the methods of synthesis provided herein. Isolated and purified and/or crystallized intermediates may also be stored for later use.

The steps and routes of synthesis are effective for preparation of a variety of GGCI salts.

Organic acids include both aliphatic and aromatic carboxylic acids and include, for example, aliphatic monocarboxylic acids, aliphatic dicarboxylic acids, aliphatic tricarboxylic acids, aromatic monocarboxylic acids, aromatic dicarboxylic acids, aromatic tricarboxylic acids and other organic acids known to those of skill in the art.

Aliphatic carboxylic acids may be saturated or unsaturated. Suitable aliphatic carboxylic acids include those having from 2 to about 10 carbon atoms.

Aliphatic monocarboxylic acids include saturated aliphatic monocarboxylic acids and unsaturated aliphatic monocarboxylic acids. Examples of saturated monocarboxylic acids include acetic acid, propronic acid, butyric acid, valeric acid, caproic acid, enanthic acid, caprylic acid, pelargonic acid, and caprynic acid. Examples of unsaturated aliphatic monocarboxylic acids include acrylic acid, propiolic acid, methacrylic acid, crotonic acid and isocrotonic acid.

Aliphatic dicarboxylic acids include saturated aliphatic dicarboxylic acids and unsaturated aliphatic dicarboxylic acids. Examples of saturated aliphatic dicarboxylic acids include oxalic acid, malonic acid, succinic acid, glutaric acid, adipic acid, pimelic acid, suberic acid, azelaic acid, and sebacic acid. Examples of unsaturated aliphatic dicarboxylic acids include maleic acid, fumaric acid, citraconic acid, mesaconic acid, itaconic acid and the like.

In certain aspects, crystalline GGCI and salts thereof are described. These include crystalline GGCI maleate, GGCI fumarate, and GGCI succinate. Different GGCI crystals include those comprising the geometric structures, unit cell structures, and structural coordinates.

Also described are GGCI salts of high purity, methods for their preparation, and dosage forms including GGCI salts.

The pharmaceutical compositions may include, for example, one or more pharmaceutically acceptable excipients, carriers, and/or additives suitable for oral or parenteral administration.

The product formed by the described processes is substantially pure, that is, substantially free from any other compounds. Preferably, it contains less than 10% impurities, and more preferably, less than about 5% impurities, and even more preferably, less than about 1% impurities. The product thus formed is also preferably substantially pure, i.e., contains less than 10% impurity, more preferably less than 5% impurity, and still more preferably less than 1% impurity. The present invention also includes a substantially pure anhydrous crystalline form of GGCI disuccinate. The term "substantially pure" means that a sample of the relevant anhydrous crystalline form of GGCI disuccinate contains more than 90% of a single polymorphic form, preferably more than 95% of a single polymorphic form, and still more preferably more than 99% of a single polymorphic form.

The synthetic methods described herein are also illustrated with reference to the figures, including accompanying FIG. 1. FIG. 1 shows a summary of an exemplary reaction scheme for the preparation of GGCI, which may include a GGCI salt.

Doses

A therapeutically effective amount of the compounds herein and their pharmaceutically acceptable salts and solvates, may be from about 1 mg/kg to about 10 g/kg. Other therapeutically effective dose ranges include, for example, from about 1.5 mg/kg to about 950 mg/kg, about 2 mg/kg to about 90 mg/kg, about 3 mg/kg to about 85 mg/kg, about 4 mg/kg to about 80 mg/kg, about 5 mg/kg to about 750 mg/kg, about 5 mg/kg to about 700 mg/kg, about 5 mg/kg to about 600 mg/kg, about 5 mg/kg to about 500 mg/kg, about 10 mg/kg to about 400 mg/kg, about 10 mg/kg to about 300 mg/kg, about 10 mg/kg to about 200 mg/kg, about 10 mg/kg to about 250 mg/kg, about 10 mg/kg to about 200 mg/kg, about 10 mg/kg to about 200 mg/kg, about 10 mg/kg to about 150 mg/kg, about 10 mg/kg to about 100 mg/kg, about 10 mg/kg to about 75 mg/kg, about 10 mg/kg to about 50 mg/kg, about 15 mg/kg to about 35 mg/kg, about 15 mg/kg to about 9500 mg/kg, about 20 mg/kg to about 900 mg/kg, about 30 mg/kg to about 850 mg/kg, about 40 mg/kg to about 800 mg/kg, about 50 mg/kg to about 7500 mg/kg, about 50 mg/kg to about 7000 mg/kg, about 50 mg/kg to about 600 mg/kg, about 5 mg/kg to about 500 mg/kg, about 100 mg/kg to about 4000 mg/kg, about 100 mg/kg to about 3000 mg/kg, about 100 mg/kg to about 2000 mg/kg, about 100 mg/kg to about 2500 mg/kg, about 100 mg/kg to about 2000 mg/kg, about 100 mg/kg to about 2000 mg/kg, about 100 mg/kg to about 1500 mg/kg, about 100 mg/kg to about 1000 mg/kg, about 100 mg/kg to about 750 mg/kg, about 100 mg/kg to about 500 mg/kg, about 150 mg/kg to about 350 mg/kg, In certain embodiments, the dose ranges include, for example, 1/10 of LD50 based on toxicity data, including for example, about 50 mg/kg to about 600 mg/kg, about 60 to about 500 mg/kg, about 70 to about 400 mg/kg, about 80 to about 300 mg/kg, about 90 to about 150 mg/kg, about 90 to about 120 mg/kg, about 95 to about 105 mg/kg, and about 100 mg/kg.

A daily dosage level of the compounds herein, and their pharmaceutically acceptable salts and solvates, may be from about 10 mg to about 6 g per day, or up to about 60 g per day (in single or divided doses). Other therapeutically effective dose ranges include, for example, from about 20 mg to about 5.9 g, from about 30 mg to about 4.7 g, from about 40 mg to about 3.5 g, from about 50 mg to about 3 g, from about 60 mg to about 2.8 g, from about 70 mg to about 2.5 g, about 80 mg to about 2.3 g, about 100 mg to about 2 g, about 100 mg to about 1.5 g, about 200 mg to about 1400 mg, about 200 mg to about 1300 mg, about 200 mg to about 1200 mg, about 200 mg to about 1100 mg, about 200 mg to about 1000 mg, about 300 mg to about 900 mg, about 300 mg to about 800, about 300 mg to about 700 mg, about 300 mg to about 600 mg, from about 200 mg to about 59 g, from about 300 mg to about 47 g, from about 400 mg to about 35 g, from about 500 mg to about 30 g, from about 600 mg to about 28 g, from about 700 mg to about 25 g, about 800 mg to about 23 g, about 1000 mg to about 20 g, about 1000 mg to about 15 g, about 2000 mg to about 14000 mg, about 2000 mg to about 13000 mg, about 2000 mg to about 12000 mg, about 2000 mg to about 11000 mg, about 2000 mg to about 10000 mg, about 3000 mg to about 9000 mg, about 3000 mg to about 8000 mg, about 3000 mg to about 7000 mg or about 3000 mg to about 6000 mg per day.

Compounds described herein, and their pharmaceutically acceptable salts and solvates, will also be effective at doses in the order of 1/10, 1/50, 1/100, 1/200, 1/300, 1/400, 1/500 and even 1/1000 of those described herein.

In some embodiments of the invention, a therapeutically effective amount is the amount effective to elicit a plasma concentration of the compounds provided herein, and their pharmaceutically acceptable salts and solvates, from about 0.01 mg/L to about 20 mg/L, about 0.01 mg/L to about 15 mg/L, about 0.1 mg/L to about 10 mg/L, about 0.5 mg/L to about 9 mg/L, about 1 mg/L to about 8 mg/L, about 2 mg/L to about 7 mg/L or about 3 mg/L to about 6 mg/L.

The doses described herein, may be administered in a single dose or multiple doses. For example, doses may be administered once, twice, three, four or more times a day, or one, two, three, four, five, or six times per week.

The physician will determine the actual dosage which will be most suitable for an individual patient, and it will vary with the age, weight and response of the particular patient. The above dosages are exemplary of the average case; there can, of course, be individual instances where higher or lower dosage ranges are merited, and such are within the scope of this invention.

Generally, in humans, IP administration of the compounds of the invention is the preferred route. A preferred oral dosing regimen in cancer treatment for a typical man is from about 400 mg to about 6000 mg per day of compound when required. Preventative doses are lower, typically from about $\frac{1}{10}$ to about $\frac{1}{20}$ of the above amounts, including from about 20-40 mg to about 40-600 mg per day.

For veterinary use, a compound provided herein, or a veterinarily acceptable salt thereof, or a veterinarily acceptable solvate of either entity, is administered as a suitably acceptable formulation.

Thus the invention provides a pharmaceutical composition comprising a GGCI compound provided herein, or a pharmaceutically acceptable salt thereof, or a pharmaceutically acceptable solvate of either entity, together with a pharmaceutically acceptable diluent or carrier.

It further provides a veterinary formulation comprising a GGCI compound provided herein, or a veterinarily acceptable salt thereof, or a veterinarily acceptable solvate of either entity, together with a veterinarily acceptable diluent or carrier.

The invention also provides a GGCI compound provided herein, or a pharmaceutically acceptable salt thereof, or a pharmaceutically acceptable solvate of either entity, or a pharmaceutical composition containing any of the foregoing, for use as a human medicament.

In addition, it provides a GGCI compound provided herein, or a veterinarily acceptable salt thereof, or a veterinarily acceptable solvate of either entity, or a veterinary formulation containing any of the foregoing, for use as an animal medicament.

In yet another aspect, the invention provides the use of a GGCI compound provided herein, or a pharmaceutically acceptable salt thereof, or a pharmaceutically acceptable solvate of either entity, for the manufacture of a human medicament for the curative or prophylactic treatment of a medical condition for which a GGCI is indicated.

It also provides the use of a GGCI compound provided herein, or a veterinarily acceptable salt thereof, or a veterinarily acceptable solvate of either entity, for the manufacture of an animal medicament for the curative or prophylactic treatment of a medical condition for which a GGCI is indicated.

Moreover, the invention includes use of the compounds and compositions provided herein for methods for treating and/or preventing, in whole or in part, various diseases, disorders and conditions, including but not limited to hyperproliferative disease such as cancer.

The invention also includes pharmaceutical compositions, including tablets and capsules and other oral delivery forms and formulations, comprising a pharmaceutically acceptable carrier and therapeutically effective amounts of a GGCI compound as provided herein.

The invention includes methods for the use of therapeutically effective amounts of a GGCI compound provided herein in the manufacture of a medicament. Such medicaments include, for example, tablets, capsules, solutions and suspensions for parenteral and oral delivery forms and formulations. Such medicaments include those for the treatment of a subject as disclosed herein.

The compounds of the invention, particularly GGCI salts, and hydrates, for example, in the disclosed crystal form, may also be prepared with another anti-cancer agent.

Doses for such GGCI compounds, salts and/or solvates as provided herein are envisaged to be administered in a therapeutically effective amount, for example, to inhibit cancer, delay tumor progression, and/or ro reduce multidrug resistance in a subject.

The invention includes a formulation comprising a GGCI compound provided herein in amounts effective to reduce glutathione transport in the body of a subject. Such formulations include, for example, tablets, capsules, solutions and suspensions for parenteral and oral delivery forms and formulations.

General Aspects of Gamma-Glutamyl Cycle

The GGC biochemical cycle exists in most living cells. It enables the transfer of amino acids, transferrin, Iron, and other moieties from outside a living cell through the cell membrane into the cytoplasm. Some such amino acids are essential for the de novo biosynthesis of glutathione. This is one of a few mechanisms that enable the transport of amino acid into living cells, but the only mechanism that is indispensable for the biosynthesis of glutathione and which does not utilize insulin as a cofactor for the transport mechanism.

Since the multiplication rate of cancerous cells is substantially higher than that of the non-cancerous cells of origin, by interfering with this cycle one can suppress cancer cell growth and maintenance. This can be achieved by presenting a competitive inhibitor such as "false metabolite" or analog of a substrate of an enzyme in the gamma-glutamyl cycle. By doing so, more damage can be introduced into the cancerous cells than to the non-cancerous cells. Moreover, a higher activity of the enzyme gamma-glutamyl transpeptidase was reported for cancerous cells. In order to suppress the gamma-glutamyl cycle, novel GGCI inhibitors, as disclosed herein, were developed that can compete with 5-oxoproline for binding to 5-oxoprolinase and thus can block the gamma-glutamyl cycle. Blocking the GGC decreases or interferes with the influx of amino acids into the cell, thus interfering with cell division and the synthesis of glutathione. Because cancerous cells need substantially more amino acids due to a much faster doubling time, this results in preferential and/or optimal damage to the cancerous cells.

Gamma-glutamyltransferase (GGT) is a key enzyme involved in glutathione metabolism, whose expression is often significantly increased in human malignancies. In the past several years, several studies focused on the possible role of GGT in tumor progression, invasion and drug resistance. The involvement of a pro-oxidant activity of GGT, besides its early recognized contributions to cellular antioxidant defenses, has been reported. GGT-derived pro-oxidants can modulate important redox-sensitive processes and functions of the cell, with particular reference to its proliferative/apoptotic balance, which has obvious and important implications in tumor progression and drug resistance. In addition, the specificity of the enzymatic reaction carried out by GGT suggests that suitable pro-drugs could be selectively metabolized (activated) by GGT expressed in tumor tissue. Accordingly, the compounds of the invention may be useful in the treatment of hyperproliferative disorders such as cancer. The compounds may inhibit tumor growth in mammals, and may be useful for treating human cancer patients.

GGT therefore plays a role as a diagnostic/prognostic marker, as well as a target for anticancer treatments.

Gamma-glutamyltransferase (GGT) is an enzyme involved in the metabolism of glutathione (gamma-glutamyl-cysteinyl-glycine; GSH), and is expressed by a wide number of cell types. GGT catalyzes the transfer of the glutamyl moiety, linked through the glutamate gamma-carboxylic acid to cysteine, to acceptor molecules including peptides, amino acids and water.

High GGT activities are present on the luminal surface of secretory and absorptive cells, including those of bile ducts, bile canaliculi and proximal tubules of the kidney, and in endothelial cells of nervous system capillaries. A dysregulated expression of GGT has been detected in various tumor types, and GGT can be associated with GSH-dependent drug-resistance mechanisms.

Being located on the outer aspect of the cell membrane, GGT catalyzes the degradation of extracellular GSH, thus favouring the recovery of constituent amino acids for subsequent intracellular GSH resynthesis. As GSH is the main water-soluble antioxidant within the cell, GGT is an important component of the cell protection system against oxidative stress. On the other hand, other pathophysiologically relevant compounds are also GGT substrates, in particular all GSH conjugates, including leukotriene C4, S-nitrosoglutathione (GSNO) and GSH adducts of xenobiotics formed by the action of glutathione-S-transferases.

Several studies showed that GGT is up-regulated in different cell types after acute exposure to oxidative stress. A connection between GGT expression and activation of Ras-MAPK pathways has been demonstrated in colon cancer cells following gamma-irradiation, as well as exposure to oxidative stress. Reactive oxygen species (ROS) have been implicated in the process of carcinogenesis, and at the same time, the redox regulation of many genes in response to ROS/electrophiles seems to modulate GGT expression; this could altogether explain the increased GGT expression described in tumors.

The distribution and concentration of GGT in human tumors present several differences from what is observed in normal tissues. Increased levels of GGT have been observed in cancer of ovary, colon, liver, astrocytic glioma, soft tissue sarcoma, melanoma, leukemias, and lung. In studies on melanoma cells in vitro and in vivo, elevated GGT activity was found to accompany an increased invasive growth, and a positive correlation was described between GGT expression and unfavourable prognostic signs in human breast cancer.

GGT Functions in the Cancer Cell

Several studies have addressed the relationships of GGT activity with the malignant phenotype, in particular the question of whether an increased GGT expression itself plays any active role in neoplastic transformation. The involvement of GGT in cellular resupply of GSH, and the increased resistance to pro-oxidant drugs observed in several GGT-expressing cell lines, indicated the inclusion of GGT among the components of cellular defensive systems. On the other hand, a number of recent findings indicate that, under particular conditions, the metabolism of GSH by GGT can exert pro-oxidant effects, with modulatory effects on several redox-sensitive processes.

Figure 2:
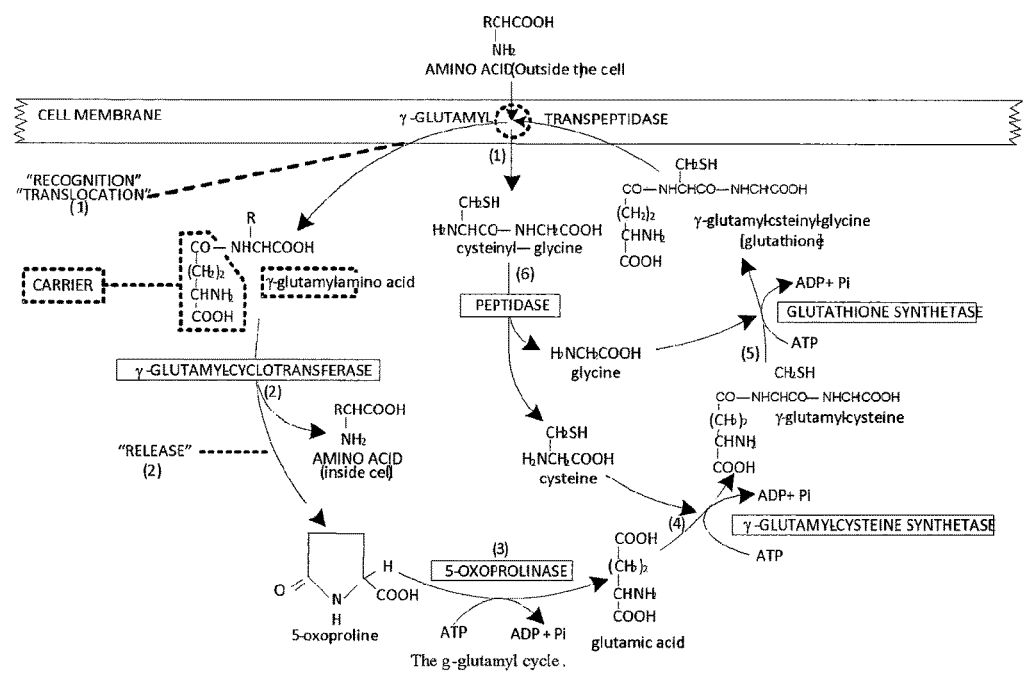
FIG. 2 is a diagram showing the GGC biochemical pathway.
Figures 3A, 3B:
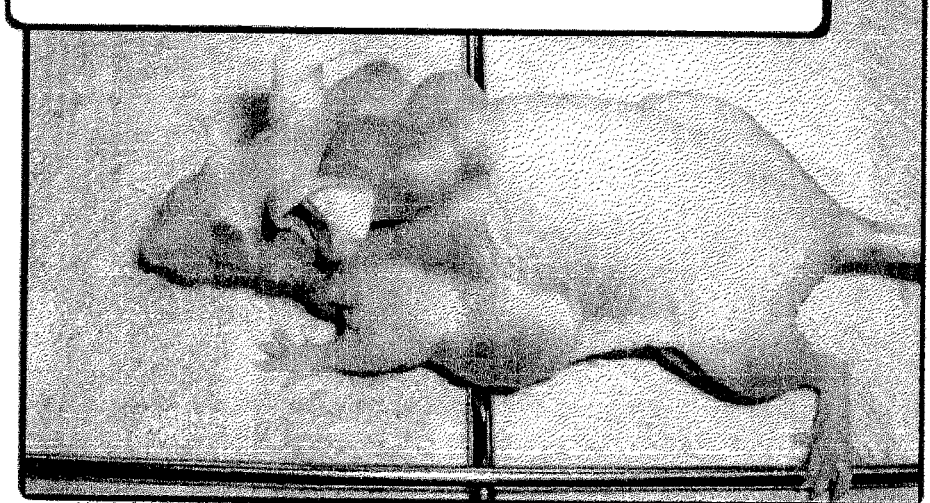
FIGS. 3A and 3B are comparative images of tumor sizes between the control group and the GGCI treated group of nude mice engrafted with human malignant melanoma.
Figure 4A:
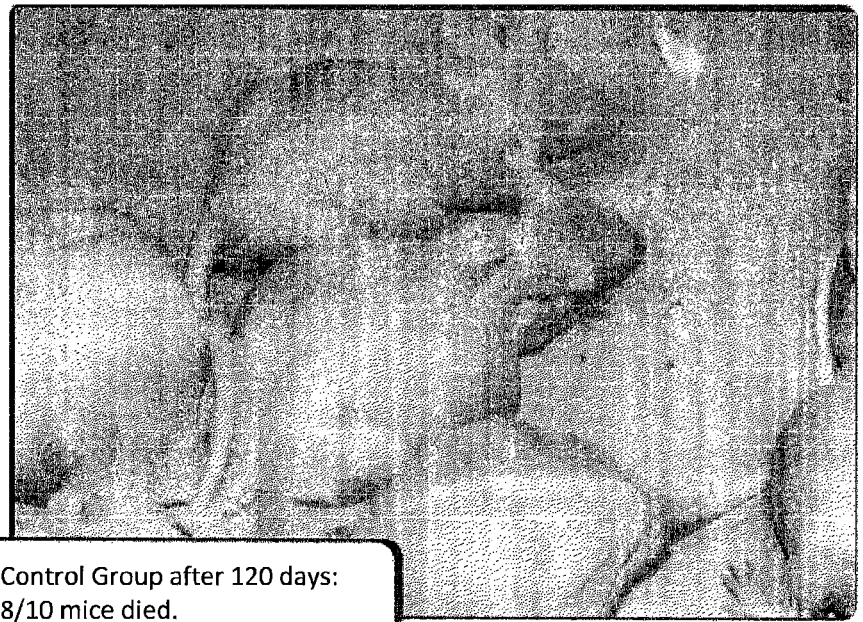
FIGS. 4A and 4B are comparative images of tumor sizes between the control group and the GGCI treated group of nude mice engrafted with human lung cancer.
Figure 4B:
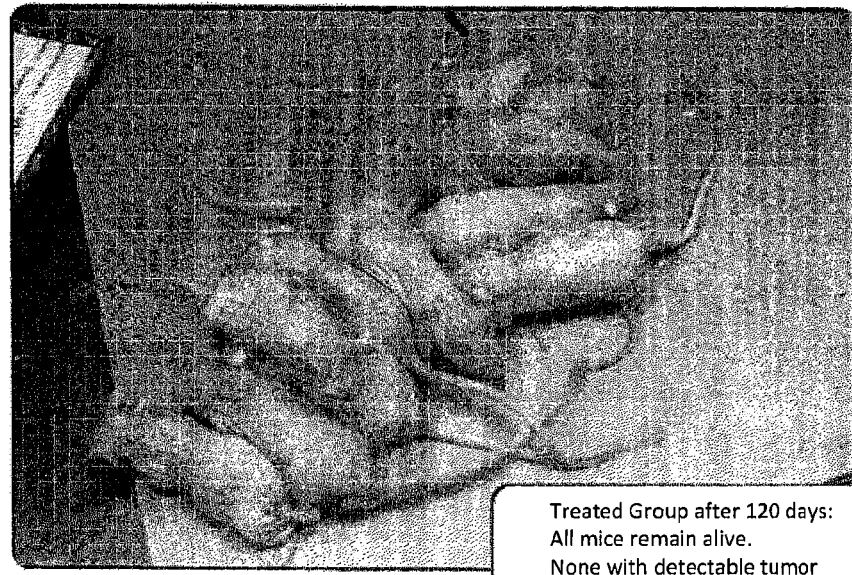

GSH is synthesized inside cells and transported in the extracellular milieu through plasma-membrane transporters, down a concentration gradient (millimolar vs. micromolar). Extracellular metabolism of GSH by GGT, in concert with cell surface dipeptidases, promotes the release and recovery by cells of constituent amino acids, among which are glutamic acid and essential cysteine. Indeed, studies performed both in vitro and in vivo showed that GGT-overexpressing cells are able to utilize extracellular GSH as a source of cysteine more efficiently, resulting in a selective growth advantage both at physiological and at limiting cysteine concentrations. It was, in fact, observed that a short (2 h) inhibition of GGT is able to lower intracellular cysteine in GGT-positive cervical carcinoma cell lines. Thus, the favouring action of GGT in tumor growth is twofold, in that it operates as a source of essential amino acids both for protein synthesis and for the maintenance of intracellular levels of GSH (FIG. 2).

Adequate levels of GSH are the basis of cellular resistance against several electrophilic/alkylating compounds, and GGT-overexpressing cells have been reported to be more resistant to hydrogen peroxide, and chemotherapics such as doxorubicin, cisplatin and 5-fluorouracil. In melanoma cells, GSH depletion and GGT inhibition significantly increased cytotoxicity of oxidative stress conditions.

GGT activity, by converting poorly reactive GSH into highly reactive cysteinyl-glycine, is able to trigger the formation of cisplatin/thiol complexes in the extracellular space, resulting in lower cellular accumulation of cisplatin, reduced DNA platination and reduced cytotoxicity.

It has been reported that GGT can exert pro-oxidant effects at the membrane surface level, and in the extracellular microenvironment. This phenomenon was explained with the high reactivity of cysteinyl-glycine, the GGT product of GSH cleavage. The lower pKa of the cysteinyl-glycine thiol makes it able to dissociate more rapidly at physiological pH, and to reduce extracellular transition metal cations (in particular $Fe^{3+}$ and $Cu^{2+}$) more efficiently than GSH itself. Iron reduction by GSH, in fact, might be limited by the chelating properties of the alpha-carboxyl group of the glutamate residue, affecting sterical and redox interactions of the cysteine thiol. GGT-catalyzed removal of glutamic acid causes a decrease of the cysteine thiol pKa and makes it free to interact with iron.

In addition, GGT activity can promote the release of free iron from transferrin, thus promoting the uptake of iron by cancer cells. This effect may play an additional role in supplying iron to malignant cells, and the role of iron in carcinogenesis is well established.

The pro-oxidant activity of GGT was also recently shown to promote the iron-dependent oxidative damage of DNA in GGT-transfected melanoma cells, thus potentially contributing to DNA damage and increased mutation risk in cancer cells.

A major role in such regulation is played by cysteine thiols, which can undergo different redox modifications, all of which possibly reflecting a distinct functional state of a protein. A number of such phenomena have been described in proteins participating in crucial cell functions, such as cell proliferation, apoptosis, cell adhesion and gene expression, whose alterations are of primary importance in progression of cancer and other diseases. GGT activity can promote the oxidation of thiol groups in cell surface proteins, a process involving hydrogen peroxide and formation of mixed disulfides ('protein S-thiolation'). The modulatory effects of GGT-mediated pro-oxidant reactions could contribute to the resistance phenotype of GGT-expressing cancer cells, by regulating both signal transduction pathways involved in proliferation/apoptosis balance, as well as by inducing protective adaptations in the pool of intracellular antioxidants.

As discussed above, the antioxidant adaptations associated with GGT expression are the basis for an increased cellular tolerance against oxidative stress, which itself is a factor of resistance to the effects of pro-oxidant drugs. Association of more agents in therapy can, however, overcome such resistance; in a recent paper, for example, the combination of arsenic trioxide with subtoxic concentrations of ascorbic acid resulted in a sensitization to apoptotic cell death of GGT-transfected/arsenic trioxide-resistant melanoma cells.

GGT expression and activity in the pathophysiology of cellular processes involving nitric oxide (NO) and related compounds, GSNO in the first place. Treatments of human cancer cells with NO and NO mimetics can effectively restore the sensitivity of resistant cell populations to the cytotoxic effects of chemotherapeutics. NO thus acts as a chemosensitizing agent. GGT selectively metabolizes GSNO, thus promoting the release of its NO load.

Methods of Administration of GGCI

The present invention is based a surprising, and unexpected, discovery that GGCI agents have the ability to modulate amino acid transport by selectively acting as analogs of 5-oxoproline and modulate the gamma-glutamyl cycle.

In addition, aspects of the present invention are based on the surprising discovery that-GGCI have the ability to treat, prevent, and/or reduce glutathione in cancer cells.

For the purpose of the current disclosure, the following definitions shall, in their entireties, be used to define technical terms, and to define the scope of the composition of matter for which protection is sought in the claims.

The instant disclosure provides methods of treatment by administration to a subject of one or more effective dose(s) of GGCI for a duration to achieve the desired therapeutic effect. The subject is preferably a mammal, including, but not limited to, animals such as cows, pigs, horses, chickens, cats, dogs, etc., and is most preferably human.

Various delivery systems are known, and can be used to administer GGCI in accordance with the methods of the invention, e.g., encapsulation in liposomes, microparticles or microcapsules. Methods of introduction include, but are not limited to, topical, subcutaneous, intradermal, intramuscular, intraperitoneal, intravenous, subcutaneous, intranasal, epidural, and oral routes. For treatment of certain cancers, topical, subcutaneous, intradermal, and systemic deliveries can be particularly efficacious.

GGCI can be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce pharmaceutical compositions comprising GGCI into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent. It may be desirable to administer the pharmaceutical compositions comprising GGCI locally to the area in need of treatment; this may be achieved, for example, and not by way of limitation, by topical application, by injection, by means of a catheter, by means of a suppository, or by means of an implant, said implant being of a porous, non-porous, or gelatinous material, including membranes, such as silastic membranes, or fibers.

Still other modes of administration of GGCI involve delivery in a controlled release system. In certain embodiments, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). Additionally polymeric materials can be used (see Medical Applications of Controlled Release, Langer and Wise (eds.), CRC Pres, Boca Raton, Fla. (1974); Controlled Drug Bioavailability, Drug Product Design and Performance, Smolen and Ball (eds.), Wiley, N.Y. (1984); Ranger and Peppas, J. Macromol. Sci. Rev. Macromol. Chem. 23:61 (1983; see also Levy et al., Science 228:190 (1985); During et al., Ann. Neurol. 25:351 (1989); Howard et al., J. Neurosurg. 71:105 (1989)), or a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)). Other controlled release systems are discussed in the review by Langer (Science 249:1527-1533 (1990)).

Forms and Dosages of GCGI

As used herein, for cancer treatment, lyophilized formulation and liquid formulation suitable for injection are particularly efficacious. Suitable dosage forms of GGCI for use in embodiments of the present invention encompass physiologically/pharmaceutically acceptable carriers that are inherently non-toxic and non-therapeutic. Examples of such carriers include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, P6N (Neumedicines, Pasadena, Ca.) and PEG. Carriers for topical or gel-based forms of GGCI polypeptides include polysaccharides, such as sodium carboxymethylcellulose or methylcellulose, polyvinylpyrrolidone, polyacrylates, polyoxyethylene-polyoxypropylene-block polymers, PEG, and wood wax alcohols. For all administrations, conventional depot forms are suitably used. Such forms include, for example, microcapsules, nanocapsules, liposomes, plasters, inhalation forms, nose sprays, sublingual tablets, and sustained-release preparations.

Suitable examples of sustained-release preparations include semipermeable matrices of solid hydrophobic polymers containing the polypeptide, which matrices are in the form of shaped articles, e.g., films, or microcapsules. Examples of sustained-release matrices include polyesters, hydrogels (for example, poly(2-hydroxyethyl-methacrylate) as described by Langer et al., supra and Langer, supra, or poly(vinylalcohol), polylactides (U.S. Pat. No. 3,773,919), copolymers of L-glutamic acid and .gamma. ethyl-L-glutamate (Sidman et al, supra), non-degradable ethylene-vinyl acetate (Langer et al., supra), degradable lactic acid-glycolic acid copolymers such as the Lupron Depot™ (injectable microspheres composed of lactic acid-glycolicacid copolymer and leuprolide acetate), and poly-D-(−)-3-hydroxybutyric acid. While polymers, such as ethylene-vinyl acetate and lactic acid-glycolic acid, enable release of molecules for over 100 days, certain hydrogels release proteins for shorter time periods. When encapsulated GGCI polypeptides remain in the body for a long time, they may denature, or aggregate, as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

In the case of administrations over several days or longer, depending on the condition, the treatment is sustained until a desired suppression of disease symptoms occurs. However, other dosage regimens may be useful. The progress of this therapy is easily monitored by conventional techniques and assays.

Therapeutic formulations of GGCI are prepared for storage by mixing GGCI, having the desired degree of purity, with optional physiologically acceptable carriers, excipients, or stabilizers (Remington's Pharmaceutical Sciences, 16th edition, Osol, A., Ed., (1980)), in the form of lyophilized cake, or aqueous solutions. Acceptable carriers, excipients, or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or non-ionic surfactants such as Tween®, Pluronics™ or polyethylene glycol (PEG).

The term "buffer", as used herein, denotes a pharmaceutically acceptable excipient, which stabilizes the pH of a pharmaceutical preparation. Suitable buffers are well known in the art and can be found in the literature. Pharmaceutically acceptable buffers include, but are not limited to, histidine-buffers, citrate-buffers, succinate-buffers, acetate-buffers, phosphate-buffers, arginine-buffers, or mixtures thereof. The abovementioned buffers are generally used in an amount of about 1 mM to about 100 mM, of about 5 mM to about 50 mM and of about 10-20 mM. The pH of the buffered solution can be at least 4.0, at least 4.5, at least 5.0, at least 5.5 or at least 6.0. The pH of the buffered solution can be less than 7.5, less than 7.0, or less than 6.5. The pH of the buffered solution can be about 4.0 to about 7.5, about 5.5 to about 7.5, about 5.0 to about 6.5, and about 5.5 to about 6.5 with an acid or a base known in the art, e.g. hydrochloric acid, acetic acid, phosphoric acid, sulfuric acid and citric acid, sodium hydroxide and potassium hydroxide. As used herein when describing pH, "about" means plus or minus 0.2 pH units.

As used herein, the term "surfactant" can include a pharmaceutically acceptable excipient which is used to protect protein formulations against mechanical stresses, like agitation and shearing. Examples of pharmaceutically acceptable surfactants include polyoxyethylensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), and sodium dodecyl sulphate (SDS). Suitable surfactants include polyoxyethylenesorbitan-fatty acid esters such as polysorbate 20, (sold under the trademark Tween 20®) and polysorbate 80 (sold under the trademark Tween 80®). Suitable polyethylene-polypropylene copolymers are those sold under the names Pluronic® F68 or Poloxamer 188®. Suitable Polyoxyethylene alkyl ethers are those sold under the trademark Brij®. Suitable alkylphenolpolyoxyethylene esthers are sold under the tradename Triton-X. When polysorbate 20 (Tween 20®) and polysorbate 80 (Tween 80®) are used, they are generally used in a concentration range of about 0.001 to about 1%, of about 0.005 to about 0.2% and of about 0.01% to about 0.1% w/v (weight/volume).

As used herein, the term "stabilizer" can include a pharmaceutically acceptable excipient, which protects the active pharmaceutical ingredient and/or the formulation from chemical and/or physical degradation during manufacturing, storage and application. Chemical and physical degradation pathways of protein pharmaceuticals are reviewed by Cleland et al., Crit. Rev. Ther. Drug Carrier Syst., 70(4):307-77 (1993); Wang, Int. J. Pharm., 7S5(2): 129-88 (1999); Wang, Int. J. Pharm., 203(1-2): 1-60 (2000); and Chi et al, Pharm. Res., 20(9): 1325-36 (2003). Stabilizers include, but are not limited to, sugars, amino acids, polyols, cyclodextrines, e.g. hydroxypropyl-beta-cyclodextrine, sulfobutylethyl-beta-cyclodextrin, beta-cyclodextrin, polyethylenglycols, e.g. PEG 3000, PEG 3350, PEG 4000, PEG 6000, albumine, human serum albumin (HSA), bovine serum albumin (BSA), salts, e.g., sodium chloride, magnesium chloride, calcium chloride, chelators, e.g., EDTA as hereafter defined. As mentioned hereinabove, stabilizers can be present in the formulation in an amount of about 10 to about 500 mM, an amount of about 10 to about 300 mM, or in an amount of about 100 mM to about 300 mM. In some embodiments, exemplary GGCI can be dissolved in an appropriate pharmaceutical formulation, wherein it is stable.

GGCI also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles, and nanocapsules), or in macroemulsions. Such techniques are disclosed in Remington's Pharmaceutical Sciences, supra.

GGCI to be used for in vivo administration must be sterile. This is readily accomplished by filtration through sterile filtration membranes, prior to, or following, lyophilization and reconstitution. GGCI ordinarily will be stored in lyophilized form, or in solution. Therapeutic GGCI compositions generally are placed into a container having a sterile access port, for example, an intravenous solution bag, or vial, having a stopper pierceable by a hypodermic injection needle.

When applied topically, GGCI is suitably combined with other ingredients, such as carriers and/or adjuvants. There are no limitations on the nature of such other ingredients, except that they must be physiologically acceptable and efficacious for their intended administration, and cannot degrade the activity of the active ingredients of the composition. Examples of suitable vehicles include ointments, creams, gels, or suspensions, with, or without, purified collagen. The compositions also may be impregnated into transdermal patches, plasters, and bandages, preferably in liquid or semi-liquid form.

For obtaining a gel formulation, GGCI formulated in a liquid composition may be mixed with an effective amount of a water-soluble polysaccharide, or synthetic polymer, such as PEG, to form a gel of the proper viscosity to be applied topically. The polysaccharide that may be used includes, for example, cellulose derivatives, such as etherified cellulose derivatives, including alkyl celluloses, hydroxyalkyl celluloses, and alkylhydroxyalkyl celluloses, for example, methylcellulose, hydroxyethyl cellulose, carboxymethyl cellulose, hydroxypropyl methylcellulose, and hydroxypropyl cellulose; starch and fractionated starch; agar; alginic acid and alginates; gum arabic; pullullan; agarose; carrageenan; dextrans; dextrins; fructans; inulin; mannans; xylans; arabinans; chitosans; glycogens; glucans; and synthetic biopolymers; as well as gums such as xanthan gum; guar gum; locust bean gum; gum arabic; tragacanth gum; and karaya gum; and derivatives and mixtures thereof. The preferred gelling agent herein is one that is inert to biological systems, nontoxic, simple to prepare, and not too runny or viscous, and will not destabilize the GGCI molecule held within it.

Preferably the polysaccharide is an etherified cellulose derivative, more preferably one that is well defined, purified, and listed in USP, e.g., methylcellulose and the hydroxyalkyl cellulose derivatives, such as hydroxypropyl cellulose, hydroxyethyl cellulose, and hydroxypropyl methylcellulose. Most preferred herein is methylcellulose.

The polyethylene glycol useful for gelling is typically a mixture of low and high molecular weight PEGs to obtain the proper viscosity. For example, a mixture of a PEG of molecular weight 400-600 with one of molecular weight 1500 would be effective for this purpose, when mixed in the proper ratio to obtain a paste.

The term "water soluble", as applied to the polysaccharides and PEGs, is meant to include colloidal solutions and dispersions. In general, the solubility of the cellulose derivatives is determined by the degree of substitution of ether groups, and the stabilizing derivatives useful herein should have a sufficient quantity of such ether groups per anhydroglucose unit in the cellulose chain to render the derivatives water soluble. A degree of ether substitution of at least 0.35 ether groups per anhydroglucose unit is generally sufficient. Additionally, the cellulose derivatives may be in the form of alkali metal salts, for example, the Li, Na, K, or Cs salts.

If methylcellulose is employed in the gel, preferably it comprises about 2-5%, more preferably about 3%, of the gel and GGCI is present in an amount of about 300-1000 mg per ml of gel.

An effective amount of GGCI to be employed therapeutically will depend, for example, upon the therapeutic objectives, the route of administration, and the condition of the patient. Accordingly, it will be necessary for the therapist to titer the dosage and modify the route of administration, as required to obtain the optimal therapeutic effect. Typically, the clinician will administer GGCI until a dosage is reached that achieves the desired effect. In certain embodiments, the appropriate dosing can be determined based on an amount of GGCI administered per surface area of the affected region.

"Near the time of administration of the treatment" refers to the administration of GGCI at any reasonable time period, either before, and/or after the administration of the treatment, such as about one month, about three weeks, about two weeks, about one week, several days, about 120 hours, about 96 hours, about 72 hours, about 48 hours, about 24 hours, about 20 hours, several hours, about one hour or minutes. Near the time of administration of the treatment may also refer to either the simultaneous, or near simultaneous, administration of the treatment and GGCI, i.e., within minutes to one day.

"Chemotherapy" refers to any therapy that includes natural or synthetic agents now known, or to be developed in the medical arts. Examples of chemotherapy include the numerous cancer drugs that are currently available. However, chemotherapy also includes any drug, natural or synthetic, that is intended to treat a disease state. In certain embodiments of the invention, chemotherapy may include the administration of several state of the art drugs intended to treat the disease state. Examples include combined chemotherapy with docetaxel, cisplatin, and 5-fluorouracil, for patients with locally advanced squamous cell carcinoma of the head (Tsukuda, M. et al., Int J Clin Oncol. 2004 June; 9 (3): 161-6), and fludarabine and bendamustine in refractory and relapsed indolent lymphoma (Konigsmann M, et al., Leuk Lymphoma. 2004; 45 (9): 1821-1827).

As used herein, exemplary sources of therapeutic or accidental ionizing radiation can include, for example, alpha, beta, gamma, x-ray, and neutron sources.

"Radiation therapy" refers to any therapy where any form of radiation is used to treat the disease state. The instruments that produce the radiation for the radiation therapy are either those instruments currently available, or to be available in the future.

"Chemoprotection or radioprotection" refers to protection from, or an apparent decrease in, the associated hematopoietic toxicity of a treatment intended to target the disease state.

"Solid tumors" generally refers to the presence of cancer of body tissues other than blood, bone marrow, or the lymphatic system.

EXAMPLES

The invention is now described with reference to the following Examples. These Examples are provided for the purpose of illustration only, and the invention is not limited to these Examples, but rather encompasses all variations that are evident as a result of the teaching provided herein.

Prior to the experiments described herein, there were no published protocol that allows for compositions and methods comprising specific GGCI 5-oxoproline analog preparation for treating cancer and other proliferative diseases. Aspects and embodiments of the instant disclosure stem from the unexpected discovery that certain GGCI formulations have surprising, and unexpected, utility and efficacy when administered to a subject.

By way of example, a method to prepare therapeutically effective radioprotective GGCI formulation was developed. The compounds of the invention were prepared, as outlined below, according to the methods described herein. However, the invention is not limited to these methods; the compounds may also be prepared as described for structurally related compounds in the literature.

Example 1: Synthesis of Exemplary Gamma Glutamyl Cycle Inhibitors (GGCI)

Exemplary GGCI compounds were synthesized according to the following synthesis schemes.

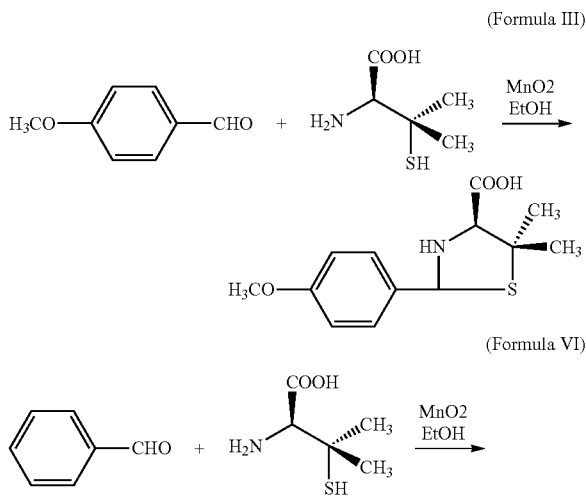

-continued

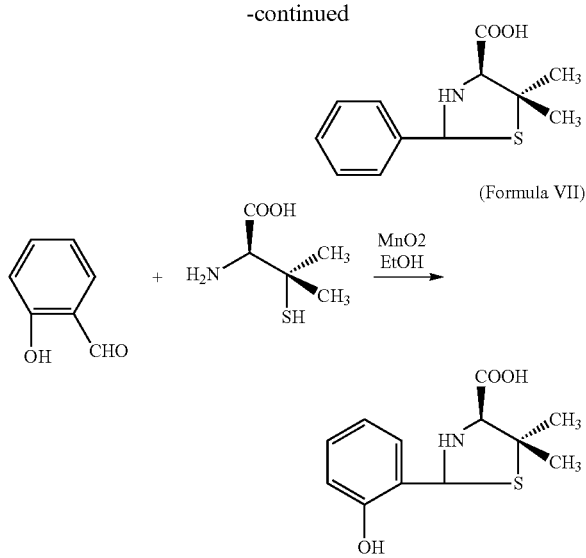

(Formula VII)

The compounds of formula-I-VII can be obtained by methods described herein and shown in FIG. 1. The compound of formula III, for example, 2-imino-3-p-methoxy-benzyl-4 sulfanyl-5 dimethyl 1-carboxylic acid, was prepared as follows: Equimolar quantities of (p-methoxybenzaldehyde), di methyl cysteine and manganese dioxide were dissolved in 2 liters of 70% ethanol. The mixture was made in a rotary evaporator and the temperature was raise to 70 degrees centigrade. After about 1 hour, all the ingredients in the mixture dissolved. The volume was then reduced by one liter. The solution was then left in the flask to cool down overnight at room temperature. The next day, the precipitating white crystals of GCL were filtered and then dried in a vacuum oven. The yield was estimated to be about 80%.

In some embodiments this invention also relates to the reaction intermediates for, or within, any of the synthesis schemes disclosed herein. The compounds of this invention may also include optical isomers, and pharmaceutically acceptable salts of any of the compounds disclosed herein.

In some embodiments, this invention also relates to products generated by the synthetic schemes disclosed herein, where L-penicillamine, L-cysteine or cystamine is used as a reactant.

Example 2: Demonstration of the Efficacy of GGCI in the Treatment of Nude Mice Inoculated with Human Melanoma In order to examine the survival rate of athymic nude mice, inoculated intravenously with tumors, one group of the inoculated mice was treated with BA-GGCI, and a second group of the inoculated mice were treated with placebo, and the effects of treatment with BA-GGCI and placebo were compared.

Two subgroups of nude mice were examined: a control group and an experimental group. The groups included a total of twenty athymic nude mice (ten control and ten experimental), each irradiated with 400 rads of radiation and inoculated with Human Melanoma cells 624 at 3.0×10,000,000 cells per mouse. Treatment of the experimental group with racemic BA-GGCI commenced at 24 hours after the inoculation. The treatment was administered intraperitoneally (I.P.) at a dose of 100 mg/kg in 2 cc of saline every day, six days a week. The control group received placebo (2 cc saline IP), every day, six days a week.

The subjects were followed up for 120 days. The results indicated that, in the Control group, ten out of ten subjects died (no survival) whereas, ten out of ten subjects in the treated group were all alive. Two of the subjects developed small tumors after stopping the treatment.

Racemic SA-GGCI and racemic PMB-GGCI were also tested, each giving results similar to those obtained with racemic BA-GGCI.

Example 3: Demonstration of the Efficacy of Using GGCI in the Treatment of Human Lung Cancer Using the Nude Mouse Model The efficacy of an exemplary GGCI in the treatment of human lung cancer, using the nude mouse model was demonstrated in a study. In order to examine survival of athymic nude mice inoculated intravenously with tumors, one group of the inoculated mice was treated with racemic BA-GGCI, and a second group of the inoculated mice were treated with placebo, and the effects of treatment with BA-GGCI and placebo were compared.

Two subgroups of nude male mice where examined: A control group and an experimental group. The groups included twenty athymic nude mice (ten control and ten experimental) subjects, each irradiated with 400 rads of radiation and inoculated with lung CA CRL5891 at 3×10,000,000 cells per mouse. Interventional treatment was identical to the first study as above.

The subjects were followed up for 120 days. In the Control group, eight of ten subjects died. Two of the surviving mice developed a large tumor. In the treated group, all mice remained alive (none with detectable tumor).

Racemic SA-GGCI and racemic PMB-GGCI were also tested, each giving results similar to those obtained with racemic BA-GGCI.

Example 4: Demonstration of Efficacy Based on Human Data

Two patients with advanced prostate cancer were treated under a compassionate use program with an exemplary GGCI Racemic BA-GGCI was administered to two human subjects who were receiving hormonal therapy for 12 and 14 months respectively. When the human subjects failed to react to the hormonal therapy, and/or any other conventional therapy, administration of the GGCI treatment began.

At the onset of the GGCI treatment, both patients were bedridden with PSA (Prostate Specific Antigen) values of 340 and 180 ng/mL respectively. Both subjects presented with multiple bone metastases, and agonizing pains. The GGCI treatment protocol comprised 600 mg of GGCI capsule 3 times/day (formulated for human based on less then 5% of the LD50 toxicity on mice). The following results were observed:

The first human patient (subject #1) presented with the following, in response to exemplary GGCI treatment: The subjects' pain level subsided within 10 days after receiving treatment. The Subject recovered enough to return to his regular activities within a month. Subject's PSA value dropped from 340 to 18 units. The PSA level continued to drop to 5 units. The bone CAT scan showed substantial remission. Subject felt normal for 28 months before he eventually passed away.

The following human patient (subject #2) presented with the following: The pains subsided after 7 days. The subject returned to his normal activities within 2-3 weeks. The subject's PSA dropped to 16 units. The subject was still alive, and feeling well, 36 months after initiation of the treatment. Subject is currently still receiving the GGCI treatment on a daily basis.

Treatment with racemic SA-GGCI gave results similar to those obtained with B-GGCI treatment, although patients to whom SA-GGCI were administered subjectively felt better than patients to whom BA-GGCI was administered.

Example 5: Demonstration of Surprising and Unexpected Efficacy Using Exemplary GGCI Prepared by FIG. 1 Synthesis Using L-Penicillamine Relative activities of the exemplary enantiomeric GGCI compounds of this invention were compared. Conjugates of benzaldehyde, salicylaldehyde and para-methoxybenzaldehyde were prepared, using either enantiomeric L- or D-penicillamine as the second reactant. The efficacy of racemic BA-GGCI, racemic SA-GGCI and racemic PMB-GGCI in the treatment of human prostate cancer was tested using the nude mouse model as in Example 2, except that the nude mice were inoculated intravenously with a human prostate tumor cell line. One group of the inoculated mice was treated with the racemic BA-GGCI and a control group of the inoculated mice was treated with placebo, and the effects of treatment with GGCI and placebo were compared. Response to treatment was monitored by changes in [PSA]. The results were similar to those obtained with other nude mouse-human tumor models, where the group of mice treated with the racemic GGCI had a significantly higher survival rate than the control group. Racemic SA-GGCI or PMB-GGCI were also tested, and gave similar results.

The exemplary L- and D-enantiomer BA-GGCIs were prepared in accordance with synthetic scheme of FIG. 1 using L-penicillamine. Preparation of the GGCI using the same synthetic scheme with D-penicillamine as starting material yielded a GGCI that had no measurable effect on the subject.

When the activity of (L)-BA-GGCI was tested compared to the corresponding racemate, the (L) compound were at least twice as active as the corresponding racemic mixture. Similar results were obtained for L-SA-GGCI and L-PMB-GGCI compared to their corresponding racemate.

Example 6: Toxicity Study, Demonstration of Safety and Efficacy

LD50 data was measured, and exemplary gamma-glutamyl cycle inhibitor's toxicity study was conducted on Balb C Mice. A conjugate of L-penicillamine and methyl glyoxal (MGPA) was administered at about 4500 mg/kg ip, 5000 mg/kg oral. A conjugate of L-penicillamine and para-methoxyphenyl (PMPA) was administered at 5250 mg/kg ip, 5500 mg/kg oral; and a conjugate of L-penicillamine and citronellal (CNPA) was administered at 3250 mg/kg ip, 4500 mg/kg oral.

Example 7: Mouse Toxicity Data

Summary of $LD_{50}$ Determination with a conjugate of L-penicillamine and salicylaldehyde (L-SAPA), a conjugate of L-penicillamine and benzaldehyde (L-BAPA), a conjugate of L-penicillamine and pyruvic aldehyde (L-PAPA) and a conjugate of L-penicillamine and glutaric dialdehyde (L-GAPA) in B6C3F$_1$ Mice.

| GGCI Compound | Schedule | Route | Calculated LD50 mg/kg/inj. | 1/10 $LD_{50}$ |
|---|---|---|---|---|
| L-SAPA | Day 1 | ip | >5000 | 500 |
|  | Day 1 | oral | >5000 | 500 |
|  | Day 1-5 | ip | 3750 | 375 |
|  | Day 1-5 | oral | >5000 | 500 |
| L-BAPA | Day 1 | ip | 884 | 88.4 |
|  | Day 1 | oral | 3553 | 355 |
|  | Day 1-5 | ip | 884 | 88.4 |
|  | Day 1-5 | oral | 2158 | 216 |
| L-PAPA | Day 1 | ip | >5000 | 500 |
|  | Day 1 | oral | >5000 | 500 |
|  | Day 1-5 | ip | 2771 | 277 |
|  | Day 1-5 | oral | >5000 | 500 |
| L-GAPA | Day 1 | ip | 3749 | 375 |
|  | Day 1 | oral | >5000 | 500 |
|  | Day 1-5 | ip | 1690 | 169 |
|  | Day 1-5 | oral | >5000 | 500 |

Example 8: Exemplary Assay for Determination of Toxicity and Demonstration of Safety in Animal Model Sample: L-Thiazolidine-di-methyl-carboxylic acid: "L-BAPA" powder was mixed in the food (pellets).

Subjects were examined for: Sub-acute (4 weeks) per os (via food) toxicity of L-BAPA to mice.

Experimental Procedure

Animals and Husbandry:

Forty females and forty male CD1 mice, 8-10 weeks old, were housed 5 per cage (milipore filtered top cages), half of them used as controls, receiving normal mouse diet (prepared at the breeding center food plant). The other half were the experimental group and received same food composition in which 0.6 g L-Thiazolidine-di-methyl-carboxylic acid in kg food was mixed and pelleted in smaller pellet machine. This food contains 12% humidity, as compared with 6% humidity of the control diet. The animals were fed ad libitum. All animals were weighed weekly and food consumption was recorded. Possible clinical or pharmaceutical effects were checked daily. After 4 weeks, the mice were put into metabolic cages for 24 hours, their urine was collected, and then the animals were bled before sacrificing. The blood was analyzed and bone marrow smears were prepared for differential count.

The reason for putting 40 mice in a group was to assure enough blood and urine for analysis, so all the blood clinical chemistry and urinalysis are of a pool of 2 mice each. All other results are individual results, performed randomly on one of each 2 mouse group.

The following organs were examined histologically: adrenals, brain, eye, gonads, heart, intestines (colon, caecum, duodenum, ileum, rectum) kidneys, liver, lungs, lymph nodes (mesenterial and inguinal) mammary gland, mediastinum, esophagus, pancreas, pituitary, salivary gland, skeletal muscle, skin, spinal cord, spleen, stomach, thyroid, urinary bladder and uterus. The organs were fixed in Bouin's solution and stained with hematoxylin-eosin-phosphomolybdic-acid light green stain. Weights for the adrenals, gonads, kidneys, liver and pituitary were recorded and the ratio organ weight/body weight was calculated.

The following lab studies were performed:

Hematology: Hemoglobin, hematocrit, erythrocyte count, leukocyte count.

Clinical chemistry: alkaline phosphatase, blood urea nitrogen, serum glutamic, pyruvic transaminase, blood sugar.

Urinalysis: appearance occult blood, protein Ph, bilirubin, ketones, glucose, nitrites, urobilinogen.

Results

During the observation and dosing period of 4 weeks, the mice were examined daily for possible clinical symptoms, but no clinical or other effect could be observed.

The results of all tests performed are summarized below:

1. Body weight: The animals ended the experiment gaining weight, and there is no significant difference between the experimental group and the control group.

2. Food consumption: From the tables we see that more L-BAPA containing experimental food was consumed by the experimental group then normal food by the control, but this is due to the fact that the humidity of the experimental food is much higher.

3. Organ weight and ratio: Organ/body weight: No significant difference between the experimental and the control group is noted. All values are within the normal values and no significant differences between the experimental and the control group is seen.

4. Blood clinical chemistry and urinalysis: All values are within the normal range and no significant difference between the control and the experimental groups is noted. (The protein traces which were noted in all mice is most probably due to slight contamination of the urine by food).

5. Blood cell analysis and differential count: All values are within the normal range and no significant difference between the control and the experimental groups is noted.

6. Bone marrow differential count: All values are within the normal range and no significant difference between the control and the experimental groups is noted.

Histopathology

Histological examinations were performed for 10 male and 10 females for each group. Thirty-one organs were examined for each animal. Cerebellar and cerebral regions of the brain looked normal, with no signs of perivascular reaction. The eyes were normal. In the testes, spermatogenesis was normally presented. In the ovaries, follicles of all stages were observed. The heart muscle and intestines were normal and the mammary gland "juvenile" and normal. Normal patterns were noted also for the lymph nodes (inguinal, mesenterial) mediastinum, esophagus, pancreas, prostate, uterus, pituitary, salivary glands, skeletal muscle, skin, spinal cord, spleen, stomach, thymus, and urinary bladder. In the kidneys, glomeruli and Bowman's capsule are nicely presented. Proximal, distal, convoluted and collecting tubuli are intact and do not contain any material. The peribronchi and alveolar areas of the lungs are clear. In the liver, the portal spaces are clear, normal looking epithelial and sinusoidal elements.

In two mice of the control, and one mouse of the experimental group, a few lipoid vacuoles in the hippocampus (artifact?) are seen. No other pathological or other changes could be observed.

CONCLUSIONS

As a demonstration of safety, L-Thiazolidine-di-methyl-carboxylic-acid ("L-BAPA") mixed in the food (0.6 g in kg food) and fed ad libitum for 4 weeks does not produce any clinical or pathological changes to mice.

Patents, patent applications, publications, scientific articles, books, web sites, and other documents and materials referenced or mentioned herein are indicative of the levels of skill of those skilled in the art to which the inventions pertain. Each such referenced document and material is hereby incorporated by reference to the same extent as if it had been incorporated by reference in its entirety individually or set forth or reprinted herein in its entirety. Additionally, all claims in this application, and all priority applications, including but not limited to original claims, are hereby incorporated in their entirety into, and form a part of, the written description of the invention. Applicants reserve the right to physically incorporate into this specification any and all materials and information from any such patents, applications, publications, scientific articles, web sites, electronically available information, and other referenced materials or documents. Applicants reserve the right to physically incorporate into any part of this document, including any part of the written description, and the claims referred to above, including, but not limited to, any original claims.

The inventions have been described broadly and generically herein. Each of the narrower species and subgeneric groupings falling within the generic disclosure also form part of these inventions. This includes the generic description of each invention which hereby include, including any claims thereto, a proviso or negative limitation removing, or optionally allowing the removal of, any subject matter from the genus, regardless of whether or not the excised materials, or options, were specifically recited or identified in haec verba herein, and all such variations form a part of the original written description of the inventions. In addition, where features, or aspects, of an invention are described in terms of a Markush group, the invention shall be understood thereby to be described in terms of each and every, and any, individual member or subgroup of members of the Markush group.

Although the invention has been described in terms of synthesis of GGCIs and GGCI salts, it should be recognized that the routes, steps, and intermediates described in the disclosure are applicable to the synthesis of CGI.

The inventions illustratively described and claimed herein can suitably be practiced in the absence of any element or elements, limitation or limitations, not specifically disclosed herein, or described herein, as essential. Thus, for example, the terms "comprising," "including," "containing," "for example", etc., shall be read expansively and without limitation. The term "including" means "including but not limited to." The phrase "for example" is not limited to, or by, the items that follow the phrase. All references to things "known in the art" include all those things and equivalents and substitutes, whether now known, or later discovered.

In claiming their inventions, the inventors reserve the right to substitute any transitional phrase with any other transitional phrase, and the inventions shall be understood to include such substituted transitions and form part of the original written description of the inventions. Thus, for example, the term "comprising" may be replaced with either of the transitional phrases "consisting essentially of" or "consisting of."

The methods and processes illustratively described herein may be suitably practiced in differing orders of steps. They are not necessarily restricted to the orders of steps indicated herein, or in the claims.

Under no circumstances may the patent be interpreted to be limited to the specific examples, or embodiments, or methods, specifically disclosed herein. Under no circumstances may the patent be interpreted to be limited by any statement made by any Examiner, or any other official or employee of the Patent and Trademark Office, unless such statement was specifically, and without qualification or reservation, expressly adopted by Applicants in a responsive writing specifically relating to the application that led to this patent prior to its issuance.

The terms and expressions employed herein have been used as terms of description and not of limitation, and there is no intention in the use of such terms and expressions, or any portions thereof, to exclude any equivalents now know or later developed, whether or not such equivalents are set forth or shown or described herein or whether or not such equivalents are viewed as predictable, but it is recognized that various modifications are within the scope of the invention claimed, whether or not those claims issued with or without alteration or amendment for any reason. Thus, it shall be understood that, although the present invention has been specifically disclosed by preferred embodiments and optional features, modifications and variations of the inventions embodied therein or herein disclosed can be resorted to by those skilled in the art, and such modifications and variations are considered to be within the scope of the inventions disclosed and claimed herein.

Specific methods and compositions described herein are representative of preferred embodiments and are exemplary of, and not intended as limitations on, the scope of the invention. Other objects, aspects, and embodiments will occur to those skilled in the art upon consideration of this specification, and are encompassed within the spirit of the invention as defined by the scope of the claims. Where examples are given, the description shall be construed to include, but not to be limited to, only those examples. It will be readily apparent to one skilled in the art that varying substitutions and modifications may be made to the invention disclosed herein, without departing from the scope and spirit of the invention, and from the description of the inventions, including those illustratively set forth herein, it is manifest that various modifications and equivalents can be used to implement the concepts of the present invention, without departing from its scope. A person of ordinary skill in the art will recognize that changes can be made in form and detail without departing from the spirit and the scope of the invention. The described embodiments are to be considered in all respects as illustrative and not restrictive. Thus, for example, additional embodiments are within the scope of the invention and within the following claims.

While this invention has been disclosed with reference to specific embodiments, it is apparent that other embodiments and variations of this invention can be devised by those skilled in the art, without departing from the true spirit and scope of the invention. The appended claims include all such embodiments and equivalent variations.

The invention claimed is:

1. A method of treating cancer comprising administering to a subject, in need thereof, a therapeutically effective amount of a pharmaceutical composition consisting essentially of a stereoisomeric compound of formula (III):

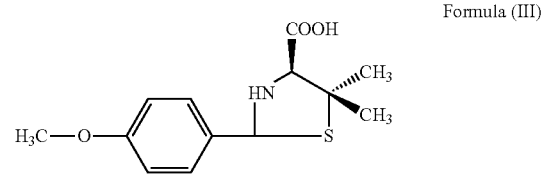

Formula (III)

or pharmaceutically acceptable salts thereof, and
a pharmaceutically acceptable carrier, diluent, or excipient.

2. The method of claim 1, wherein the compound of formula (III) is given in one or more doses ranging from about 700 mg/kg to about 7.0 g/kg for each dose.

3. The method of claim 2, wherein each dose ranges from about 3.0 g/kg to about 6.0 g/kg.

4. The method of claim 1, wherein the cancer is a solid tumor.

5. The method of claim 4, wherein the solid tumor comprises sarcomas, carcinomas, or lymphomas.

6. The method of claim 1, wherein the cancer is selected from the group consisting of lung, breast, prostate, pancreatic, ovarian, bladder, head and neck, thyroid, brain, skin and kidney.

\* \* \* \* \*